(12) United States Patent
Nemes

(10) Patent No.: US 10,775,339 B2
(45) Date of Patent: Sep. 15, 2020

(54) MEMBRANES FOR USE IN ELECTROCHEMICAL SENSORS AND ASSOCIATED DEVICES

(71) Applicant: Gentex Corporation, Zeeland, MI (US)

(72) Inventor: Joel C. Nemes, Holland, MI (US)

(73) Assignee: GENTEX CORPORATION, Zeeland, MI (US)

(*) Notice: Subject to any disclaimer, the term of this patent is extended or adjusted under 35 U.S.C. 154(b) by 718 days.

(21) Appl. No.: 14/946,485

(22) Filed: Nov. 19, 2015

(65) Prior Publication Data

US 2016/0146751 A1    May 26, 2016

Related U.S. Application Data

(60) Provisional application No. 62/084,888, filed on Nov. 26, 2014.

(51) Int. Cl.
| | | |
|---|---|---|
| *G01N 27/404* | (2006.01) | |
| *G01N 27/407* | (2006.01) | |

(Continued)

(52) U.S. Cl.
CPC ..... *G01N 27/4045* (2013.01); *G01N 27/4074* (2013.01); *H01M 8/0293* (2013.01);
(Continued)

(58) Field of Classification Search
CPC ........... G01N 27/4045; G01N 27/4074; G01N 33/004; H01M 8/0293; H01M 8/1041;
(Continued)

(56) References Cited

U.S. PATENT DOCUMENTS

| | | | |
|---|---|---|---|
| 4,329,214 A | | 5/1982 | Spritzer et al. |
| 4,337,141 A | * | 6/1982 | Watanabe ............. B01D 61/44 |
| | | | 204/296 |

(Continued)

OTHER PUBLICATIONS

Yoshiro Kaneko "Preparation of Ionic Polysilsesquioxanes with Regular Structures and Their Ion-Exchange Behaviors" Intech, 2012.*

(Continued)

*Primary Examiner* — Michael Y Sun
(74) *Attorney, Agent, or Firm* — Foley & Lardner LLP; Bradley D. Johnson

(57) ABSTRACT

A membrane is provided, as well as membrane electrode assemblies and sensors utilizing the membrane of the present technology. The membrane includes a membrane material with a top surface and a bottom surface; and a protonic ionic liquid disposed at least between the top surface and the bottom surface of the membrane material where the protonic ionic liquid is of Formula I.

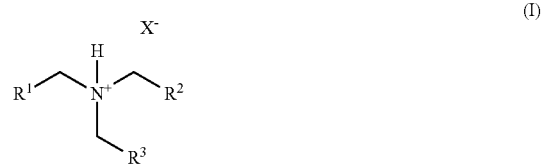

(I)

20 Claims, 8 Drawing Sheets

(51) Int. Cl.

| | |
|---|---|
| *G01N 33/00* | (2006.01) |
| *H01M 8/1041* | (2016.01) |
| *H01M 8/0293* | (2016.01) |
| *C08J 5/22* | (2006.01) |
| *C08G 61/12* | (2006.01) |
| *H01M 8/103* | (2016.01) |
| *H01M 8/1048* | (2016.01) |
| *B01D 61/44* | (2006.01) |
| *C25B 13/04* | (2006.01) |

(52) U.S. Cl.
CPC .......... *H01M 8/1041* (2013.01); *B01D 61/44* (2013.01); *C08G 61/12* (2013.01); *C08G 61/122* (2013.01); *C08G 61/123* (2013.01); *C08G 2261/3221* (2013.01); *C08G 2261/3241* (2013.01); *C08G 2261/334* (2013.01); *C08J 5/2206* (2013.01); *C08J 5/2256* (2013.01); *C08J 2325/04* (2013.01); *C08J 2379/06* (2013.01); *C25B 13/04* (2013.01); *G01N 33/004* (2013.01); *H01M 8/103* (2013.01); *H01M 8/1048* (2013.01); *Y02A 20/134* (2018.01)

(58) Field of Classification Search
CPC ..... H01M 8/1048; H01M 8/103; C25B 13/04; Y02A 20/134; B01D 61/44; C08G 2261/334; C08G 61/122; C08G 61/12; C08G 61/123; C08G 2261/3241; C08G 2261/3221; C08J 2379/06; C08J 5/2256; C08J 2325/04; C08J 5/2206
See application file for complete search history.

(56) References Cited

U.S. PATENT DOCUMENTS

| | | | |
|---|---|---|---|
| 5,211,984 A | 5/1993 | Wilson | |
| 5,302,274 A | 4/1994 | Tomantschger et al. | |
| 5,331,310 A | 7/1994 | Stetter et al. | |
| 5,573,648 A | 11/1996 | Shen et al. | |
| 5,618,493 A | 4/1997 | Goldstein et al. | |
| 5,650,054 A | 7/1997 | Shen et al. | |
| 5,944,969 A | 8/1999 | Scheffler et al. | |
| 5,958,200 A | 9/1999 | Kessel | |
| 6,172,759 B1 | 1/2001 | Goldstein | |
| 6,200,443 B1 | 3/2001 | Shen et al. | |
| 6,936,147 B2 | 8/2005 | Prohaska et al. | |
| 6,948,352 B2 | 9/2005 | Rabbett et al. | |
| 7,022,213 B1 | 4/2006 | Austen et al. | |
| 7,077,938 B1 | 7/2006 | Austen et al. | |
| 7,236,095 B2 | 6/2007 | Smith et al. | |
| 7,279,081 B2 | 10/2007 | Maeno et al. | |
| 8,623,189 B2 | 1/2014 | Eckhardt et al. | |
| 8,641,878 B2 | 2/2014 | Nemes | |
| 2005/0145494 A1 | 7/2005 | Inoue et al. | |
| 2006/0091007 A1 | 5/2006 | Inoue et al. | |
| 2006/0120924 A1 | 6/2006 | Inoue et al. | |
| 2006/0196770 A1 | 9/2006 | Tomohiro et al. | |
| 2013/0175168 A1* | 7/2013 | Nemes | G01N 27/4045 204/415 |
| 2016/0151009 A1* | 6/2016 | Rudmann | G01N 21/3504 600/322 |

OTHER PUBLICATIONS

Young Gun Ko "Primary, secondary, and tertiary amines for CO2 capture: Designing for mesoporous CO2 adsorbents" Journal of Colloid and Interface Science 361 (2011) 594-602.*

Navoroj S, Culler R, Koenig JL, Ishida H. "Structure and adsorption characteristics of silane coupling agents on silica and E-glass fiber; dependence on pH." J Colloid Interf Sci 1984;97:309-17. (Year: 1984).*

Lee et al., "Fabrication of protic ionic liquid/sulfonated polyimide composite membranes for non-humidified fuel cells," Journal of Power Sources, 195, 2010, pp. 5909-5914.

Xiao et al., "Synthesis and Characterization of Pyridine-Based Polybenzimidazoles for High Temperature Polymer Electrolyte Membrane Fuel Cell Applications," Fuel Cells 2005, 5, No. 2, pp. 287-295.

Etcheverry et al; Glass Fiber Reinforced Polypropylene Mechanical Properties Enhancement by Adhesion Improvement; 1084-1113; Jun. 18, 2012.

Grot; PDL Fluorocarbon Series; Fluorinated Ionomers; 11 pages; 2008.

Hickner et al; Alternative Polymer Systems for Proton Exchange Membranes (PEMs); 4587-4611; Feb. 27, 2004.

Zhang et al; Recent Development of Polymer Electrolyte Membranes for Fuel Cells; 53 pages ; 2012.

* cited by examiner

MEMBRANES FOR USE IN ELECTROCHEMICAL SENSORS AND ASSOCIATED DEVICES

CROSS-REFERENCE TO RELATED APPLICATIONS

This application claims priority to U.S. Provisional Patent Application No. 62/084,888, filed Nov. 26, 2014, the entire disclosure of which is hereby incorporated by reference in its entirety for any and all purposes.

FIELD

The present technology relates in general to membranes for use in electrochemical sensors. Such sensors include electrochemical gas sensors, such as carbon monoxide detectors including the membranes of the present technology. The membranes of the present technology are non-volatile, non-aqueous proton conducting membranes that are relatively unaffected by changes in relative humidity.

SUMMARY

In an aspect, a membrane is provided that includes a membrane material with a top surface and a bottom surface; and a protonic ionic liquid disposed at least between the top surface and the bottom surface of the membrane material; wherein the protonic ionic liquid is of Formula I:

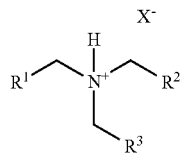

where $R^1$, $R^2$, and $R^3$ are each independently H or a substituted or unsubstituted alkyl or cycloalkyl group, or where $R^1$ and $R^2$ taken together are a $C_2$-$C_4$ alkylene group; and $X^-$ is a sulfate, bisulfate, sulfonate, halide, carboxylate, phosphate, phosphonate, dicyanamide anion, perfluoroalkylsulfonate, perfluoroalkylsulfonamide anion, or bis(perfluoroalkylsulfonyl)imide anion. In some embodiments, $R^1$, $R^2$, and $R^3$ are each independently H or an unsubstituted alkyl group. In some embodiments, $R^1$, $R^2$, and $R^3$ are each independently H, methyl, ethyl, n-propyl, or i-propyl. In some embodiments, $R^1$ and $R^2$ are each independently methyl; and $R^3$ is H.

In any of the above embodiments, $X^-$ may be a sulfonate, triflate, perfluoroalkylsulfonate, hexafluorophosphate, or triflamide anion. In any of the above embodiments, $X^-$ may be triflate, nonafluorobutylsulfonate, or a perfluoroalkylsulfonate, or $X^-$ is a sulfonate functional group of the membrane.

In any of the above embodiments, the membrane material may include one or more of an expanded polytetrafluoroethylene (PTFE), a polypropylene, a glass fiber membrane material, a cellulose membrane material, a polystyrene, a polyamide, a polybenzimidazole, or a tetrafluoroethylene-perfluoroalkylvinylether; wherein the expanded PTFE, polypropylene, polystyrene, polyamide, polybenzimidazole, and/or tetrafluoroethylene-perfluoroalkylvinylether optionally includes sulfonic acid groups, carboxylate groups, phosphate groups, phosphonate groups, or combinations of any two or more thereof.

In any of the above embodiments, the membrane may include a glass fiber membrane material. In any of the above embodiments, the glass fiber membrane material includes glass fibers and at least one structural unit according to Formula IIa:

wherein $R^4$ and $R^5$ are each independently H or a substituted or unsubstituted alkyl or cycloalkyl group, or where $R^4$ and $R^5$ taken together are a $C_4$-$C_6$ alkylene group; $R^6$ is a substituted or unsubstituted alkylene or cycloalkylene group; $R^7$ is hydroxyl, alkoxy, aryloxy, or $G^2$; $R^8$ is hydroxyl, alkoxy, aryloxy, or $G^3$; $G^1$, $G^2$, and $G^3$ are each independently an oxygen atom of the glass fiber, where $G^1$, $G^2$, and $G^3$ are not the same oxygen atom; and $Y^-$ is a sulfate, bisulfate, sulfonate, halide, carboxylate, phosphate, phosphonate, dicyanamide, perfluoroalkylsulfonate, or bis(perfluoroalkylsulfonyl)imide anion. In any of the above embodiments, the glass fiber membrane material may include at least one structural unit according to Formula IIb:

In any of the above embodiments, it may be that $R^4$ and $R^5$ are each independently H or a substituted or unsubstituted alkyl or cycloalkyl group, or where $R^4$ and $R^5$ taken together are a $C_4$-$C_6$ alkylene group; and $R^6$ is a substituted or unsubstituted alkylene or cycloalkylene group. In any of the above embodiments, it may be that $R^4$ and $R^5$ are each independently H or an unsubstituted alkyl or cycloalkyl group; and $R^6$ is an unsubstituted alkylene or cycloalkylene group. In any of the above embodiments, it may be that $R^4$ and $R^5$ are each independently H or an unsubstituted alkyl group; and $R^6$ is an unsubstituted alkylene group. In any of the above embodiments, it may be that $R^4$ and $R^5$ are each independently H or an unsubstituted alkyl group; $R^6$ is an unsubstituted alkylene group; $R^7$ is alkoxy or $G^2$; and $R^8$ is alkoxy or $G^3$. In any of the above embodiments, it may be that the glass fiber membrane material includes a plurality of structural units according to Formula IIa. In any of the above embodiments, it may be that the glass fiber membrane material includes a plurality of structural units according to Formula IIb.

In any of the above embodiments, it may be that a thickness defined by the top surface and the bottom surface of the membrane material is from about 10 μm to about 400

μm. In any of the above embodiments, it may be that the membrane has from about 20 wt % to about 90 wt % of the protonic ionic liquid. In any of the above embodiments, it may be that the membrane further includes an ion conducting material not of Formula I. In any of the above embodiments, it may be that the membrane does not include a polymer. In any of the above embodiments, it may be that the membrane is an ion exchange membrane.

In an aspect, a membrane electrode assembly is provided that includes an anode; a cathode that includes an oxygen reduction catalyst; and any of the above embodiments of the membrane.

In an aspect, an electrochemical carbon monoxide sensor for use in a gas or fire detector is provided. The sensor includes a first sidewall; a second sidewall; a top wall; and a bottom wall; the first sidewall, the second sidewall, the top wall and the bottom wall defining a containment region and containing therein a membrane electrode assembly; where the top wall includes a gaseous diffusion aperture; the membrane electrode assembly includes an anode, a cathode, and any of the above embodiments of the membrane; where the membrane permits ion transport between the anode and the cathode, the membrane prevents electron conduction between the anode and the cathode; the cathode includes an oxygen reduction catalyst. In some embodiments of the sensor, the containment region is void of a solvent reservoir. In some embodiments of the sensor, the electrochemical carbon monoxide sensor is configured to be exposed to a sample gas during a normal sensing operation; and the anode and cathode are configured to be exposed to the same sample gas at the same time during the normal sensing operation.

In any of the above embodiments of the membrane electrode assembly or the sensor, the oxygen reduction catalyst may include a pyrolysis product of a carbonaceous material and a coordination complex, the coordination complex including a transition metal and a nitrogen-containing macrocycle; where the oxygen reduction catalyst does not materially exhibit catalytic activity for the oxidation of carbon monoxide.

In some embodiments, the coordination complex is a transition metal porphyrin, a transition metal tetrabenzoporphyrin, a transition metal tetraphenylporphyrin, a transition metal tetraazaporphyrin, a transition metal tetraazamacrocycle, a transition metal phthalocyanine, a transition metal naphthalocyanine, a transition metal bis(phthalocyanine), a transition metal bis(naphthalocyanine), a ion metal bis(naphthalocyanines), or a combination of any two or more thereof. In some embodiments, the coordination complex is a cobalt porphyrin, a cobalt tetrabenzoporphyrin, a cobalt tetraphenylporphyrin, a cobalt tetraazaporphyrin, a cobalt tetraazamacrocycle, a cobalt metal phthalocyanine, a cobalt naphthalocyanine, a cobalt bis(phthalocyanine), a cobalt bis(naphthalocyanine), or a combination of any two or more thereof. In some embodiments, the coordination complex includes a compound of a transition metal ligated by a tetraazamacrocycle.

In some embodiments, the coordination complex is a compound represented by Formula III-VII, or a combination of any two or more thereof:

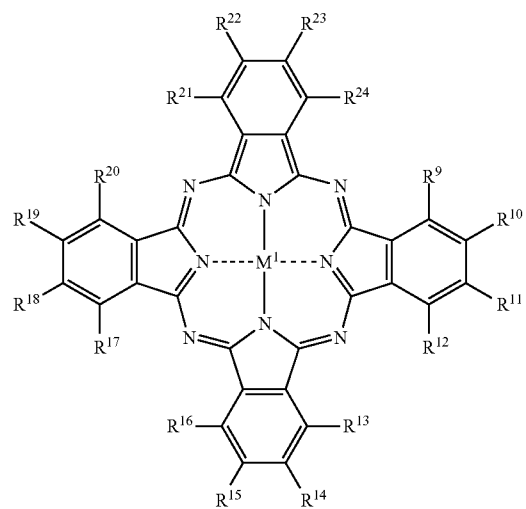

(III)

where $M^1$ is Co, Cu, Fe, Ir, Ni, Pd, Rh, Ru, or Zn; $R^9$-$R^{24}$ are each independently H, $NO_2$, $NH_2$, an amine, $CO_2H$, an ester, a $C_1$-$C_{10}$ alkyl, an ether, SH, or a thioether

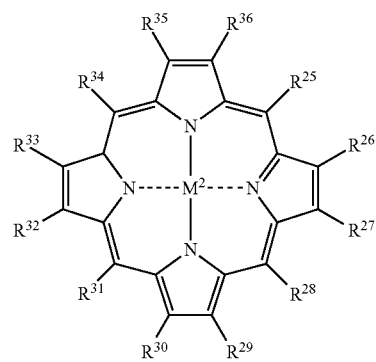

(IV)

where $M^2$ is Co, Cu, Fe, Ir, Ni, Pd, Rh, Ru, or Zn; $R^{25}$-$R^{36}$ are each independently H, $NO_2$, $NH_2$, an amine, $CO_2H$, an ester, a $C_1$-$C_{10}$ alkyl, an ether, SH, or a thioether;

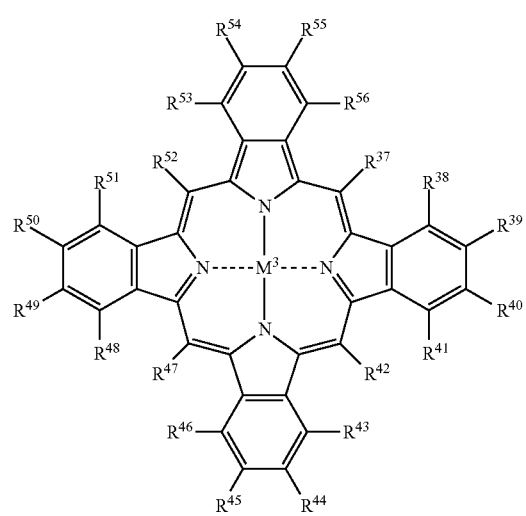

(V)

where $M^3$ is Co, Cu, Fe, Ir, Ni, Pd, Rh, Ru, or Zn; $R^{37}$-$R^{56}$ are each independently H, $NO_2$, $NH_2$, an amine, $CO_2H$, an ester, a $C_1$-$C_{10}$ alkyl, an ether, SH, or a thioether;

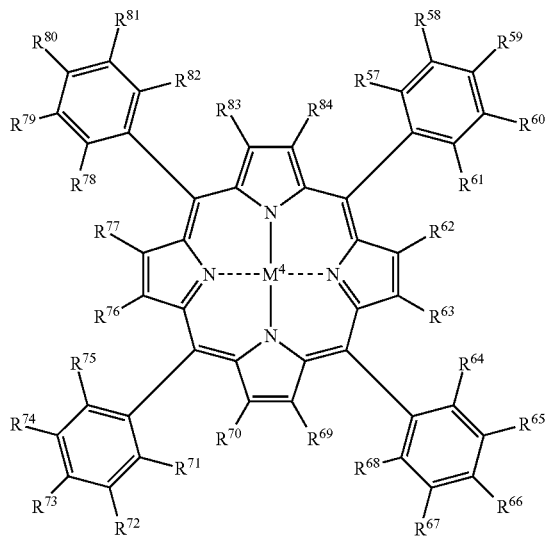

(VI)

where $M^4$ is Co, Cu, Fe, Ir, Ni, Pd, Rh, Ru, or Zn; $R^{57}$-$R^{84}$ are each independently H, $NO_2$, $NH_2$, an amine, $CO_2H$, an ester, a $C_1$-$C_{10}$ alkyl, an ether, SH, or a thioether; and

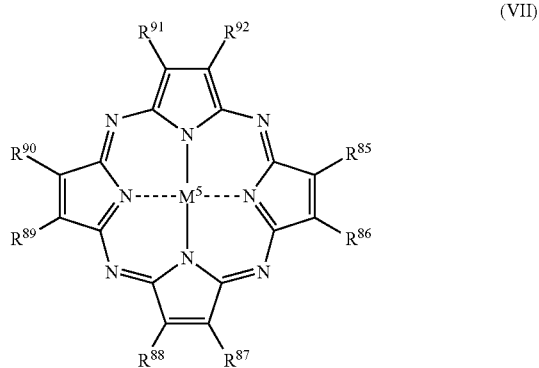

(VII)

where $M^5$ is Co, Cu, Fe, Ir, Ni, Pd, Rh, Ru, or Zn; $R^{85}$-$R^{92}$ are each independently H, $NO_2$, $NH_2$, an amine, $CO_2H$, an ester, a $C_1$-$C_{10}$ alkyl, an ether, SH, or a thioether.

In some embodiments, the coordination complex is a compound represented by Formula III. In some embodiments, the coordination complex is a compound represented by Formula III, $M^1$ is Co, and $R^9$-$R^{24}$ are each independently H. In some embodiments, the coordination complex is a compound represented by Formula III, $M^1$ is Co; and $R^9$-$R^{24}$ are each independently H, $NO_2$, or $NH_2$. In some embodiments, the coordination complex is a compound represented by Formula III, $M^1$ is Co; and $R^9$-$R^{24}$ are each independently H or $NH_2$. In some embodiments, the coordination complex is a compound represented by Formula III, $M^1$ is Co; and $R^9$-$R^{24}$ are each independently H or $NO_2$. In some embodiments, the coordination complex is a compound represented by Formula III, $M^1$ is Co; $R^{11}$, $R^{15}$, $R^{19}$, and $R^{23}$ are each independently $NH_2$; and $R^9$, $R^{10}$, $R^{12}$, $R^{13}$, $R^{14}$, $R^{16}$, $R^{17}$, $R^{18}$, $R^{20}$, $R^{21}$, $R^{22}$, and $R^{24}$ are each independently H. In some embodiments, the coordination complex is a compound represented by Formula III, $M^1$ is Co; $R^{11}$, $R^{15}$, $R^{19}$, and $R^{23}$ are each independently $NO_2$; and $R^9$, $R^{10}$, $R^{12}$, $R^{13}$, $R^{14}$, $R^{16}$, $R^{17}$, $R^{18}$, $R^{20}$, $R^{21}$, $R^{22}$, and $R^{24}$ are each independently H.

In any of the above embodiments of the membrane electrode assembly or the sensor, the carbonaceous material may include graphene, graphite, amorphous carbon, carbon nanotubes, carbon fibers, or a combination of any two or more thereof.

In any of the above embodiments of the membrane electrode assembly or the sensor, the membrane may be compressed and have a thickness of about 10 μm to about 250 μm. In any of the above embodiments of the membrane electrode assembly or the sensor, the membrane may be compressed and have a thickness of about 75 μm to about 200 μm.

In any of the above embodiments of the sensor, the sensor may further include a desiccant for retaining a liquid. In such embodiments, the liquid may include water.

DETAILED DESCRIPTION

Figure 1:
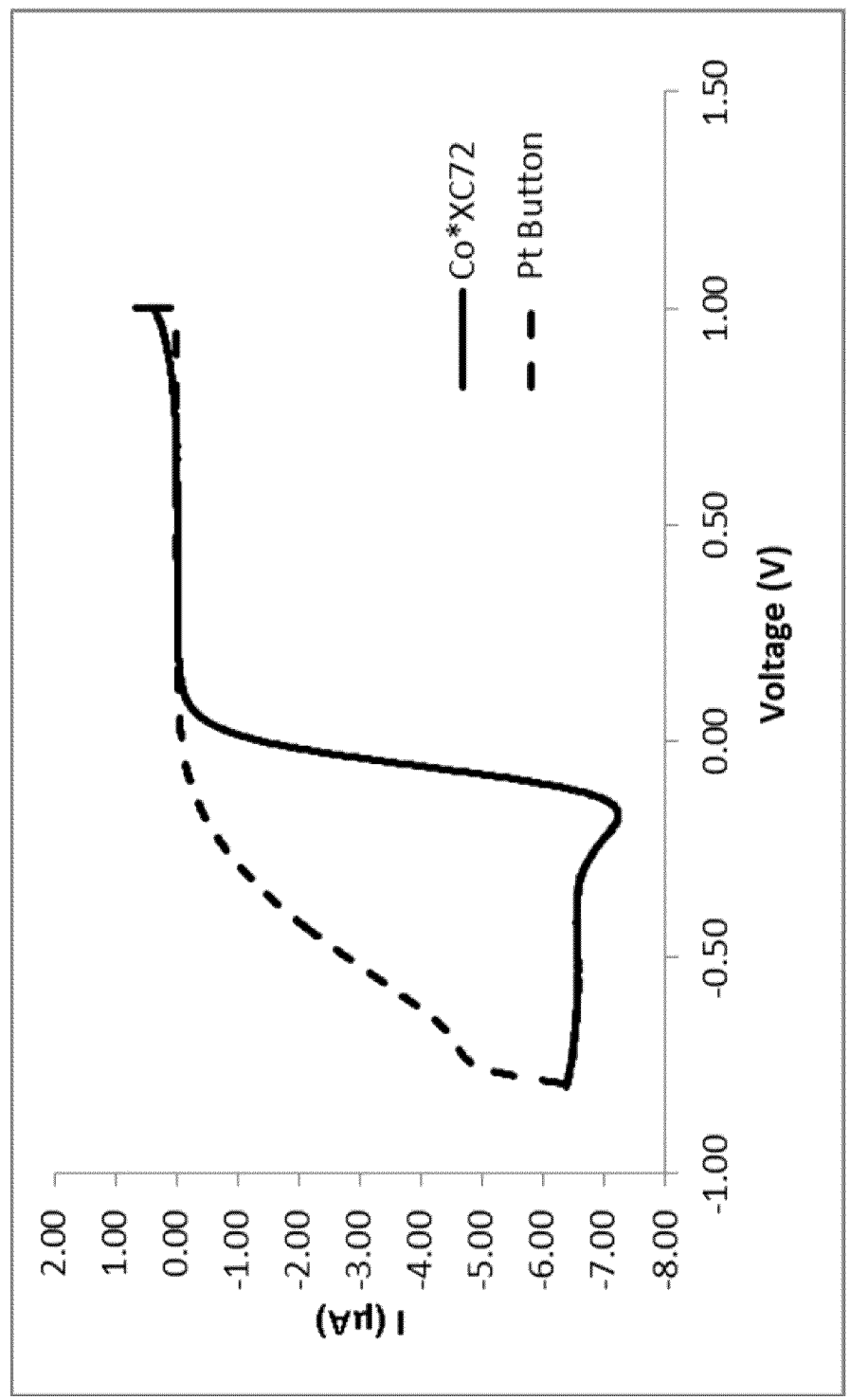
FIG. 1 illustrates the initial activity for the reduction of oxygen in a protonic ionic liquid of the present technology for a cobalt and a platinum catalyst, according to a working example.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group is substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, aryloxy, aralkyloxy, cycloalkoxy, heterocyclyloxy, and heterocyclylalkoxy groups; carbonyls (oxo); carboxylates; esters; urethanes; oximes; hydroxylamines; alkoxyamines; aralkoxyamines; thiols; sulfides; sulfoxides; sulfones; sulfonyls; pentafluorosulfanyl (i.e., $SF_5$), sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN); and the like.

Substituted ring groups such as substituted cycloalkyl, aryl, heterocyclyl and heteroaryl groups also include rings and ring systems in which a bond to a hydrogen atom is replaced with a bond to a carbon atom. Therefore, substituted cycloalkyl, aryl, heterocyclyl and heteroaryl groups may also be substituted with substituted or unsubstituted alkyl, alkenyl, and alkynyl groups as defined below.

Alkyl groups include straight chain and branched chain alkyl groups having from 1 to 12 carbon atoms (i.e., a $C_1$-$C_{12}$ alkyl group), and typically from 1 to 10 carbons (i.e., a $C_1$-$C_{10}$ alkyl group) or, in some embodiments, from 1 to 8, 1 to 6, or 1 to 4 carbon atoms. Examples of straight chain alkyl groups include groups such as methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, tert-butyl, neopentyl, isopentyl, and 2,2-dimethylpropyl groups. Representative substituted alkyl groups may be substituted one or more times with substituents such as those listed above, and include without limitation haloalkyl (e.g., trifluoromethyl), hydroxyalkyl, thioalkyl, aminoalkyl, alkylaminoalkyl, dialkylaminoalkyl, alkoxyalkyl, carboxyalkyl, and the like.

Cycloalkyl groups include mono-, bi- or tricyclic alkyl groups having from 3 to 12 carbon atoms in the ring(s), or, in some embodiments, 3 to 10, 3 to 8, or 3 to 4, 5, or 6 carbon atoms. Exemplary monocyclic cycloalkyl groups include, but not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Bi- and tricyclic ring systems include both bridged cycloalkyl groups and fused rings, such as, but not limited to, bicyclo[2.1.1] hexane, adamantyl, decalinyl, and the like. Substituted cycloalkyl groups may be substituted one or more times with, non-hydrogen and non-carbon groups as defined above. However, substituted cycloalkyl groups also include rings that are substituted with straight or branched chain alkyl groups as defined above. Representative substituted cycloalkyl groups may be mono-substituted or substituted more than once, such as, but not limited to, 2,2-, 2,3-, 2,4- 2,5- or 2,6-disubstituted cyclohexyl groups, which may be substituted with substituents such as those listed above.

Cycloalkylalkyl groups are alkyl groups as defined above in which a hydrogen or carbon bond of an alkyl group is replaced with a bond to a cycloalkyl group as defined above. In some embodiments, cycloalkylalkyl groups have from 4 to 16 carbon atoms, 4 to 12 carbon atoms, and typically 4 to 10 carbon atoms. Substituted cycloalkylalkyl groups may be substituted at the alkyl, the cycloalkyl or both the alkyl and cycloalkyl portions of the group. Representative substituted cycloalkylalkyl groups may be mono-substituted or substituted more than once, such as, but not limited to, mono-, di- or tri-substituted with substituents such as those listed above.

Alkenyl groups include straight and branched chain alkyl groups as defined above, except that at least one double bond exists between two carbon atoms. Alkenyl groups have from 2 to 12 carbon atoms, and typically from 2 to 10 carbons or, in some embodiments, from 2 to 8, 2 to 6, or 2 to 4 carbon atoms. In some embodiments, the alkenyl group has one, two, or three carbon-carbon double bonds. Examples include, but are not limited to vinyl, allyl, —CH=CH($CH_3$), —CH=C($CH_3$)$_2$, —C($CH_3$)=$CH_2$, —C($CH_3$)=CH($CH_3$), —C($CH_2CH_3$)=$CH_2$, among others. Representative substituted alkenyl groups may be mono-substituted or substituted more than once, such as, but not limited to, mono-, di- or tri-substituted with substituents such as those listed above.

Cycloalkenyl groups include cycloalkyl groups as defined above, having at least one double bond between two carbon atoms. In some embodiments the cycloalkenyl group may have one, two or three double bonds but does not include aromatic compounds. Cycloalkenyl groups have from 4 to 14 carbon atoms, or, in some embodiments, 5 to 14 carbon atoms, 5 to 10 carbon atoms, or even 5, 6, 7, or 8 carbon atoms. Examples of cycloalkenyl groups include cyclohexenyl, cyclopentenyl, cyclohexadienyl, cyclobutadienyl, and cyclopentadienyl.

Cycloalkenylalkyl groups are alkyl groups as defined above in which a hydrogen or carbon bond of the alkyl group is replaced with a bond to a cycloalkenyl group as defined above. Substituted cycloalkenylalkyl groups may be substituted at the alkyl, the cycloalkenyl or both the alkyl and cycloalkenyl portions of the group. Representative substituted cycloalkenylalkyl groups may be substituted one or more times with substituents such as those listed above.

Alkynyl groups include straight and branched chain alkyl groups as defined above, except that at least one triple bond exists between two carbon atoms. Alkynyl groups have from 2 to 12 carbon atoms, and typically from 2 to 10 carbons or, in some embodiments, from 2 to 8, 2 to 6, or 2 to 4 carbon atoms. In some embodiments, the alkynyl group has one, two, or three carbon-carbon triple bonds. Examples include, but are not limited to —C≡CH, —C≡CCH$_3$, —CH$_2$C≡CCH$_3$, —C≡CCH$_2$CH(CH$_2$CH$_3$)$_2$, among others. Representative substituted alkynyl groups may be mono-substituted or substituted more than once, such as, but not limited to, mono-, di- or tri-substituted with substituents such as those listed above.

Aryl groups are cyclic aromatic hydrocarbons that do not contain heteroatoms. Aryl groups herein include monocyclic, bicyclic and tricyclic ring systems. Thus, aryl groups include, but are not limited to, phenyl, azulenyl, heptalenyl, biphenyl, fluorenyl, phenanthrenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. In some embodiments, the aryl groups are phenyl or naphthyl. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

Aralkyl groups are alkyl groups as defined above in which a hydrogen or carbon bond of an alkyl group is replaced with a bond to an aryl group as defined above. In some embodiments, aralkyl groups contain 7 to 16 carbon atoms, 7 to 14 carbon atoms, or 7 to 10 carbon atoms. Substituted aralkyl groups may be substituted at the alkyl, the aryl or both the alkyl and aryl portions of the group. Representative aralkyl groups include but are not limited to benzyl and phenethyl groups and fused (cycloalkylaryl)alkyl groups such as 4-indanylethyl. Representative substituted aralkyl groups may be substituted one or more times with substituents such as those listed above.

Heterocyclyl groups include aromatic (also referred to as heteroaryl) and non-aromatic ring compounds containing 3 or more ring members, of which one or more is a heteroatom such as, but not limited to, N, O, and S. In some embodiments, the heterocyclyl group contains 1, 2, 3 or 4 heteroatoms. In some embodiments, heterocyclyl groups include mono-, bi- and tricyclic rings having 3 to 16 ring members, whereas other such groups have 3 to 6, 3 to 10, 3 to 12, or 3 to 14 ring members. Heterocyclyl groups encompass aromatic, partially unsaturated and saturated ring systems, such as, for example, imidazolyl, imidazolinyl and imidazolidinyl groups. The phrase "heterocyclyl group" includes fused ring species including those comprising fused aromatic and non-aromatic groups, such as, for example, benzotriazolyl, 2,3-dihydrobenzo[1,4]dioxinyl, and benzo[1,3]dioxolyl. The phrase also includes bridged polycyclic ring systems containing a heteroatom such as, but not limited to, quinuclidyl. However, the phrase does not include heterocyclyl groups that have other groups, such as alkyl, oxo or halo groups, bonded to one of the ring members. Rather, these are referred to as "substituted heterocyclyl groups".

Heterocyclyl groups include, but are not limited to, aziridinyl, azetidinyl, pyrrolidinyl, imidazolidinyl, pyrazolidinyl, thiazolidinyl, tetrahydrothiophenyl, tetrahydrofuranyl, dioxolyl, furanyl, thiophenyl, pyrrolyl, pyrrolinyl, imidazolyl, imidazolinyl, pyrazolyl, pyrazolinyl, triazolyl, tetrazolyl, oxazolyl, isoxazolyl, thiazolyl, thiazolinyl, isothiazolyl, thiadiazolyl, oxadiazolyl, piperidyl, piperazinyl, morpholinyl, thiomorpholinyl, tetrahydropyranyl, tetrahydrothiopyranyl, oxathiane, dioxyl, dithianyl, pyranyl, pyridyl, pyrimidinyl, pyridazinyl, pyrazinyl, triazinyl, dihydropyridyl, dihydrodithiinyl, dihydrodithionyl, homopiperazinyl, quinuclidyl, indolyl, indolinyl, isoindolyl, azaindolyl(pyrrolopyridyl), indazolyl, indolizinyl, benzotriazolyl, benzimidazolyl, benzofuranyl, benzothiophenyl, benzthiazolyl, benzoxadiazolyl, benzoxazinyl, benzodithiinyl, benzoxathiinyl, benzothiazinyl, benzoxazolyl, benzothiazolyl, benzothiadiazolyl, benzo[1,3]dioxolyl, pyrazolopyridyl, imidazopyridyl (azabenzimidazolyl), triazolopyridyl, isoxazolopyridyl, purinyl, xanthinyl, adeninyl, guaninyl, quinolinyl, isoquinolinyl, quinolizinyl, quinoxalinyl, quinazolinyl, cinnolinyl, phthalazinyl, naphthyridinyl, pteridinyl, thianaphthyl, dihydrobenzothiazinyl, dihydrobenzofuranyl, dihydroindolyl, dihydrobenzodioxinyl, tetrahydroindolyl, tetrahydroindazolyl, tetrahydrobenzimidazolyl, tetrahydrobenzotriazolyl, tetrahydropyrrolopyridyl, tetrahydropyrazolopyridyl, tetrahydroimidazopyridyl, tetrahydrotriazolopyridyl, and tetrahydroquinolinyl groups. Representative substituted heterocyclyl groups may be mono-substituted or substituted more than once, such as, but not limited to, pyridyl or morpholinyl groups, which are 2-, 3-, 4-, 5-, or 6-substituted, or disubstituted with various substituents such as those listed above.

Heteroaryl groups are aromatic ring compounds containing 5 or more ring members, of which, one or more is a heteroatom such as, but not limited to, N, O, and S. Heteroaryl groups include, but are not limited to, groups such as pyrrolyl, pyrazolyl, triazolyl, tetrazolyl, oxazolyl, isoxazolyl, thiazolyl, pyridinyl, pyridazinyl, pyrimidinyl, pyrazinyl, thiophenyl, benzothiophenyl, furanyl, benzofuranyl, indolyl, azaindolyl (pyrrolopyridinyl), indazolyl, benzimidazolyl, imidazopyridinyl (azabenzimidazolyl), pyrazolopyridinyl, triazolopyridinyl, benzotriazolyl, benzoxazolyl, benzothiazolyl, benzothiadiazolyl, imidazopyridinyl, isoxazolopyridinyl, thianaphthyl, purinyl, xanthinyl, adeninyl, guaninyl, quinolinyl, isoquinolinyl, tetrahydroquinolinyl, quinoxalinyl, and quinazolinyl groups. Heteroaryl groups include fused ring compounds in which all rings are aromatic such as indolyl groups and include fused ring compounds in which only one of the rings is aromatic, such as 2,3-dihydro indolyl groups. Although the phrase "heteroaryl groups" includes fused ring compounds, the phrase does not include heteroaryl groups that have other groups bonded to one of the ring members, such as alkyl groups. Rather, heteroaryl groups with such substitution are referred to as "substituted heteroaryl groups." Representative substituted heteroaryl groups may be substituted one or more times with various substituents such as those listed above.

Heterocyclylalkyl groups are alkyl groups as defined above in which a hydrogen or carbon bond of an alkyl group is replaced with a bond to a heterocyclyl group as defined above. Substituted heterocyclylalkyl groups may be substituted at the alkyl, the heterocyclyl or both the alkyl and heterocyclyl portions of the group. Representative heterocyclyl alkyl groups include, but are not limited to, morpholin-4-yl-ethyl, furan-2-yl-methyl, imidazol-4-yl-methyl, pyridin-3-yl-methyl, tetrahydrofuran-2-yl-ethyl, and indol-2-yl-propyl. Representative substituted heterocyclylalkyl groups may be substituted one or more times with substituents such as those listed above.

Heteroaralkyl groups are alkyl groups as defined above in which a hydrogen or carbon bond of an alkyl group is replaced with a bond to a heteroaryl group as defined above. Substituted heteroaralkyl groups may be substituted at the alkyl, the heteroaryl or both the alkyl and heteroaryl portions of the group. Representative substituted heteroaralkyl groups may be substituted one or more times with substituents such as those listed above.

Groups described herein having two or more points of attachment (i.e., divalent, trivalent, or polyvalent) within the compound of the present technology are designated by use of the suffix, "ene." For example, divalent alkyl groups are alkylene groups, divalent aryl groups are arylene groups, divalent heteroaryl groups are divalent heteroarylene groups, and so forth. Substituted groups having a single point of attachment to the compound of the present technology are not referred to using the "ene" designation. Thus, e.g., chloroethyl is not referred to herein as chloroethylene.

Alkoxy groups are hydroxyl groups (—OH) in which the bond to the hydrogen atom is replaced by a bond to a carbon atom of a substituted or unsubstituted alkyl group as defined above. Examples of linear alkoxy groups include but are not limited to methoxy, ethoxy, propoxy, butoxy, pentoxy, hexoxy, and the like. Examples of branched alkoxy groups include but are not limited to isopropoxy, sec-butoxy, tert-butoxy, isopentoxy, isohexoxy, and the like. Examples of cycloalkoxy groups include but are not limited to cyclopropyloxy, cyclobutyloxy, cyclopentyloxy, cyclohexyloxy, and the like. Representative substituted alkoxy groups may be substituted one or more times with substituents such as those listed above.

The terms "alkanoyl" and "alkanoyloxy" as used herein can refer, respectively, to —C(O)-alkyl groups and —O—C(O)-alkyl groups, each containing 2-5 carbon atoms.

The terms "aryloxy" and "arylalkoxy" refer to, respectively, a substituted or unsubstituted aryl group bonded to an oxygen atom and a substituted or unsubstituted aralkyl group bonded to the oxygen atom at the alkyl. Examples include but are not limited to phenoxy, naphthyloxy, and benzyloxy. Representative substituted aryloxy and arylalkoxy groups may be substituted one or more times with substituents such as those listed above.

The term "carboxylate" as used herein refers to a —COOH group. A "substituted carboxylate" refers to a —C(O)O-G where G is a carboxylate protecting group. Carboxylate protecting groups are well known to one of ordinary skill in the art. An extensive list of protecting groups for the carboxylate group functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for any and all purposes as if fully set forth herein.

The term "ester" as used herein refers to —COOR$^{170}$ groups. R$^{170}$ is a substituted or unsubstituted alkyl, cycloalkyl, alkenyl, alkynyl, aryl, aralkyl, heterocyclylalkyl or heterocyclyl group as defined herein.

The term "amide" (or "amido") includes C- and N-amide groups, i.e., —C(O)NR$^{171}$R$^{172}$, and —NR$^{171}$C(O)R$^{172}$ groups, respectively. R$^{171}$ and R$^{172}$ are independently hydrogen, or a substituted or unsubstituted alkyl, alkenyl, alkynyl, cycloalkyl, aryl, aralkyl, heterocyclylalkyl or heterocyclyl group as defined herein. Amido groups therefore include but are not limited to carbamoyl groups (—C(O)NH$_2$) and formamide groups (—NHC(O)H). In some embodiments, the amide is —NR$^{171}$C(O)—(C$_{1-5}$alkyl) and the group is termed "carbonylamino," and in others the amide is —NHC(O)-alkyl and the group is termed "alkanoylamino."

The term "nitrile" or "cyano" as used herein refers to the —CN group.

Urethane groups include N- and O-urethane groups, i.e., —NR$^{173}$C(O)OR$^{174}$ and —OC(O)NR$^{173}$R$^{174}$ groups, respectively. R$^{173}$ and R$^{174}$ are independently a substituted or unsubstituted alkyl, alkenyl, alkynyl, cycloalkyl, aryl, aralkyl, heterocyclylalkyl, or heterocyclyl group as defined herein. R$^{173}$ may also be H.

The term "amine" (or "amino") as used herein refers to —NR$^{175}$R$^{176}$ groups, wherein R$^{175}$ and R$^{176}$ are independently hydrogen, or a substituted or unsubstituted alkyl, alkenyl, alkynyl, cycloalkyl, aryl, aralkyl, heterocyclylalkyl or heterocyclyl group as defined herein. In some embodiments, the amine is alkylamino, dialkylamino, arylamino, or alkylarylamino. In other embodiments, the amine is NH$_2$, methylamino, dimethylamino, ethylamino, diethylamino, propylamino, isopropylamino, phenylamino, or benzylamino.

The term "sulfonamido" includes S- and N-sulfonamide groups, i.e., —SO$_2$NR$^{178}$R$^{179}$ and —NR$^{178}$SO$_2$R$^{179}$ groups, respectively. R$^{178}$ and R$^{179}$ are independently hydrogen, or a substituted or unsubstituted alkyl, alkenyl, alkynyl, cycloalkyl, aryl, aralkyl, heterocyclylalkyl, or heterocyclyl group as defined herein. Sulfonamido groups therefore include but are not limited to sulfamoyl groups (—SO$_2$NH$_2$). In some embodiments herein, the sulfonamido is —NHSO$_2$-alkyl and is referred to as the "alkylsulfonylamino" group.

The term "thiol" refers to —SH groups, while sulfides include —SR$^{180}$ groups, sulfoxides include —S(O)R$^{181}$ groups, sulfones include —SO$_2$R$^{182}$ groups, and sulfonyls include —SO$_2$OR$^{183}$. R$^{180}$, R$^{181}$, R$^{182}$, and R$^{183}$ are each independently a substituted or unsubstituted alkyl, cycloalkyl, alkenyl, alkynyl, aryl aralkyl, heterocyclyl or heterocyclylalkyl group as defined herein. In some embodiments the sulfide is an alkylthio group, —S-alkyl.

The term "urea" refers to —NR$^{184}$—C(O)—NR$^{185}$R$^{186}$ groups. R$^{184}$, R$^{185}$, and R$^{186}$ groups are independently hydrogen, or a substituted or unsubstituted alkyl, alkenyl, alkynyl, cycloalkyl, aryl, aralkyl, heterocyclyl, or heterocyclylalkyl group as defined herein.

The term "amidine" refers to —C(NR$^{187}$)NR$^{188}$R$^{189}$ and —NR$^{187}$C(NR$^{188}$)R$^{189}$, wherein R$^{187}$, R$^{188}$, and R$^{189}$ are each independently hydrogen, or a substituted or unsubstituted alkyl, cycloalkyl, alkenyl, alkynyl, aryl aralkyl, heterocyclyl or heterocyclylalkyl group as defined herein.

The term "guanidine" refers to —NR$^{190}$C(NR$^{191}$)NR$^{192}$R$^{193}$, wherein R$^{190}$, R$^{191}$, R$^{192}$ and R$^{193}$ are each independently hydrogen, or a substituted or unsubstituted alkyl, cycloalkyl, alkenyl, alkynyl, aryl aralkyl, heterocyclyl or heterocyclylalkyl group as defined herein.

The term "enamine" refers to —C(R$^{194}$)=C(R$^{195}$)NR$^{196}$R$^{197}$ and —NR$^{194}$C(R$^{195}$)=C(R$^{196}$)R$^{197}$, wherein R$^{194}$, R$^{195}$, R$^{196}$ and R$^{197}$ are each independently hydrogen, a substituted or unsubstituted alkyl, cycloalkyl, alkenyl, alkynyl, aryl aralkyl, heterocyclyl or heterocyclylalkyl group as defined herein.

The term "halogen" or "halo" as used herein refers to bromine, chlorine, fluorine, or iodine. In some embodiments, the halogen is fluorine. In other embodiments, the halogen is chlorine or bromine.

The term "hydroxy' as used herein can refer to —OH or its ionized form, —O$^-$.

The term "imide" refers to —C(O)NR$^{198}$C(O)R$^{199}$, wherein R$^{198}$ and R$^{199}$ are each independently hydrogen, or a substituted or unsubstituted alkyl, cycloalkyl, alkenyl, alkynyl, aryl aralkyl, heterocyclyl or heterocyclylalkyl group as defined herein.

The term "imine" refers to —CR$^{200}$(NR$^{201}$) and —N(CR$^{200}$R$^{201}$) groups, wherein R$^{200}$ and R$^{201}$ are each independently hydrogen or a substituted or unsubstituted alkyl, cycloalkyl, alkenyl, alkynyl, aryl aralkyl, heterocyclyl or heterocyclylalkyl group as defined herein, with the proviso that R$^{200}$ and R$^{201}$ are not both simultaneously hydrogen.

The term "nitro" as used herein refers to an —NO$_2$ group.

The term "trifluoromethyl" as used herein refers to —CF$_3$.

The term "trifluoromethoxy" as used herein refers to —OCF$_3$.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

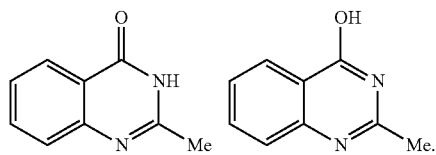

As another example, guanidines may exhibit the following isomeric forms in protic organic solution, also referred to as tautomers of each other:

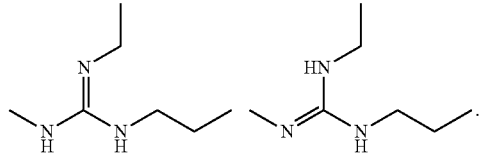

Because of the limits of representing compounds by structural formulas, it is to be understood that all chemical formulas of the compounds described herein represent all tautomeric forms of compounds and are within the scope of the present technology.

Those of skill in the art will also appreciate that compounds of the present technology may exhibit the phenomena of acid-base equilibria. As the formula drawings within the specification and claims can represent only one of the possible equilibrium species, it should be understood that the present technology encompasses any equilibrium species of the compounds having one or more of the utilities described herein, as well as mixtures of these various different species. For example, a mixture of triethylamine and sulfuric acid (H$_2$SO$_4$) exhibit an acid-base equilibrium, as represented by two equilibrium species below:

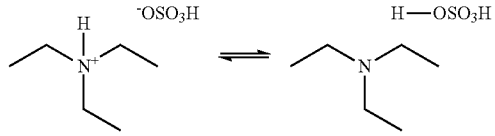

While a particular equilibrium species might predominate, such a formula drawing also encompasses the minor equilibrium species, e.g., drawing the major equilibrium species of the protonated form of triethylamine and the bisulfate ion (HSO$_4^-$) also encompasses minor equilibrium species of the non-protonated triethylamine and H$_2$SO$_4$.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

Modern fuel cells and electrochemical sensors commonly use carbon supported noble metal catalysts, such as platinum, at both the anode and the cathode. The anode typically catalyzes the oxidation of the fuel, such as hydrogen, methanol, and/or carbon monoxide. The cathode typically catalyzes the reduction of oxygen. For example, the chemical reactions that typically occur in an electrochemical carbon monoxide sensor are provided below:

Anode: $CO + H_2O \rightarrow CO_2 + 2H^+ + 2e^-$

Cathode: $\frac{1}{2}O_2 + 2H^+ + 2e^- \rightarrow H_2O$

Net: $CO + \frac{1}{2}O_2 \rightarrow CO_2$

Such fuel cells and electrochemical sensors, e.g., a carbon monoxide sensor, require an ion exchange membrane between the anode and the cathode to operate. The ions are typically protons, although other ions such as carbonates or hydroxides may also be used.

Examples of ion exchange membranes include membranes involving a polymer, such as a polyfluorinated sulfonic acid, sulfonated polyamide, and polystyrene sulfonates, or composites of these materials on an inert support such as expanded polytetrafluoroethylene (ePTFE), glass fibers, or cellulose. However, such membranes require a high level of humidity to maintain a high ionic conductivity. Moreover, they require the humidity level to be stable in order to limit changes in the ionic conductivity and a resulting variation in sensor output at a set concentration of CO. Thus, sensors employing such ion exchange membranes require a reservoir containing water. Yet because these sensors must be open to the environment to sample gas, the water is susceptible to evaporation over time eventually resulting in sensor failure. A second type of ion exchange membranes employ an inert support as described above with a strong acid, such as $H_2SO_4$ or $H_3PO_4$. These type of ion exchange membranes do not require a reservoir with water, but suffer from the highly hygroscopic nature of the strong acid at high humidity levels. This can cause leakage from the ion exchange membrane onto sensitive materials in the sensor if adequate measures to retain the additional volume (due to moisture absorption) are not employed. Such additional measures require additional materials and cost. A third type of ion exchange membrane involves acid doped polymers, such as $H_3PO_4$ doped polybenzimidazoles (PBIs) or composites of the acid doped polymers on the previously described inert supports. While this third type of ion exchange membrane does not require a reservoir with water, they are also hygroscopic and susceptible to varied ionic conductivity with changes in relative humidity. Moreover, this third type suffers from low ionic conductivity at low temperatures.

The present technology provides membranes that are non-volatile, non-aqueous proton conducting membranes that are relatively unaffected by changes in relative humidity. The membranes are electrochemically stable within the potential window which sensors typically operate, and maintain good levels of ionic conductivity within temperatures of about 0° C. to about 49° C., more preferably within temperatures of about −40° C. to about 70° C. The phrase "good levels of ionic conductivity" at least means that there is a measurable difference in signal in a sensor due to a change in CO concentration from about 0 ppm to about 30 ppm or from about 0 ppm to about 70 ppm. The present technology also relates to fuel cells and electrochemical sensors employing the membranes of the present technology, where the anode and the cathode of an associated membrane electrode assembly (MEA) are disposed upon the same side or different sides of the membrane, and/or exposed to the same gaseous environment or different gaseous environments, among other configurations. The present technology also relates to gas, smoke and/or fire detectors including the membranes, as well as associated methods of manufacturing.

Thus, in an aspect, a membrane is provided where the membrane includes a membrane material with a top surface and a bottom surface; and a protonic ionic liquid disposed at least between the top surface and the bottom surface of the membrane material, where the protonic ionic liquid is of Formula I:

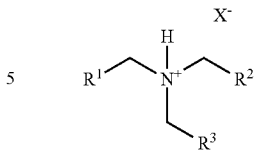

where $R^1$, $R^2$, and $R^3$ are each independently H or a substituted or unsubstituted alkyl or cycloalkyl group, or where $R^1$ and $R^2$ taken together are a $C_2$-$C_4$ alkylene group; and $X^-$ is a sulfate, bisulfate, sulfonate, halide, carboxylate, dicyanamide anion, phosphate, phosphonate, perfluoroalkylsulfonate, perfluoroalkylsulfonamide anion, or bis(perfluoroalkylsulfonyl)imide anion. It is to be understood that $X^-$ may be, but is not limited to, a sulfate, sulfonate, carboxylate, phosphate, phosphonate, perfluoroalkylsulfonate, perfluoroalkylsulfonamide anion, or bis(perfluoroalkylsulfonyl)imide anion functional group of the membrane material. The protonic ionic liquid is preferably liquid within the entire range of about 0° C. to about 49° C. and may be liquid outside of this range.

$R^1$, $R^2$, and $R^3$ may each be the same, each be different, or two of $R^1$, $R^2$, and $R^3$ the same and the remaining one different. $R^1$, $R^2$, and $R^3$ may each independently be H or an unsubstituted alkyl group. In some embodiments, $R^1$, $R^2$, and $R^3$ are each independently H, methyl, ethyl, n-propyl, or i-propyl. In some embodiments, $R^1$ and $R^2$ are each independently methyl; and $R^3$ is H. $X^-$ may be a sulfate, bisulfate, sulfonate, carboxylate, phosphate, perfluoroalkylsulfonate, or bis(perfluoroalkylsulfonyl)imide anion. In some embodiments, $X^-$ is sulfonate, triflate, hexafluorophosphate, a perfluoroalkylsulfonate, or triflamide anion, or $X^-$ is a sulfonate functional group of the membrane material. In some embodiments, $X^-$ is a sulfonate, triflate, perfluoroalkylsulfonate, or hexafluorophosphate. In some embodiments, $X^-$ is triflate or nonafluorobutylsulfonate, or $X^-$ is a sulfonate functional group of the membrane.

The membrane generally permits proton or other ion transport, such as between an anode and a cathode, but generally prevents electron conduction between the same. Non-limiting examples of suitable membrane materials include, for example, expanded PTFE (e.g., Gore, Porex), glass fibers (e.g., glass fiber membranes (Whatman, Pall, VWR), glass wool), cellulose, polystyrene sulfonic acid (from, e.g., Sigma-Aldrich), a tetrafluoroethylene-perfluoroalkylvinylether copolymer wherein the copolymer includes sulfonic acid groups (e.g., Nafion, Dupont), carboxylate groups (e.g., Flemion, Asahi Glass), phosphate groups, phosphonate groups, or a combination of any two or more thereof. Thus, in any of the embodiments of the membrane described herein, the membrane material may include one or more of an expanded polytetrafluoroethylene, a polypropylene, a glass fiber membrane material, a cellulose membrane material, a polystyrene, a polyamide, a polybenzimidazole, or a tetrafluoroethylene-perfluoroalkylvinylether, wherein the expanded PTFE, polypropylene, polystyrene, polyamide, polybenzimidazole, and/or tetrafluoroethylene-perfluoroalkylvinylether optionally includes sulfonic acid groups, carboxylate groups, phosphate groups, phosphonate groups, or combinations of any two or more thereof. Polypropylene, polystyrene, and/or polyamide, when not including such optional groups, are preferably porous, where such pores may be from about 0.2 μm to about 10 μm in diameter. Thus, the pore sizes for porous polypropylene, porous polystyrene, and/or porous polyamide may independently be for each membrane material about 0.2 μm, 0.4 μm, about 0.6 μm, about 0.8 μm, about 1.0 μm, about 1.5 μm, about 2.0 μm, about 2.5 μm, about 3.0 μm, about 3.5 μm, about 4.0 μm, about 4.5 μm, about 5.0 μm, about 5.5 μm, about 6.0 μm, about 6.5 μm, about 7.0 μm, about 7.5 μm, about 8.0 μm, about 8.5 μm, about 9.0 μm, about 9.5 μm, about 10 μm, or any range including and in between any two of these values.

In addition to the protonic ionic liquid of the present technology, the membrane may also be infused with one or more ion conducting materials not of Formula I. Such ion conducting materials include mineral acids such as $H_2SO_4$ and/or $H_3PO_4$, aqueous alkaline salts such as KOH, $H_3PO_4$ doped polybenzimidazole derivatives (L. Xiao, et al., *Fuel Cells* 5 (2005) 287), protic ionic liquid doped polybenzimidazole derivatives, and protic ionic liquid doped sulfonated polyimide derivatives (S.-Y. Lee, et al., *J. Power Sources* (2009).

In any of the embodiments of the membrane described herein, a thickness defined by the top surface and the bottom surface of the membrane material may about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, or about 400 μm as well as any range including and in between any two of these values.

As described above, the membrane may include a glass fiber membrane material. In any embodiment including a glass fiber membrane material, the glass fiber membrane material may include glass fibers and at least one structural unit according to Formula IIa:

where $R^4$ and $R^5$ are each independently H or a substituted or unsubstituted alkyl or cycloalkyl group, or where $R^4$ and $R^5$ taken together are a $C_4$-$C_6$ alkylene group; $R^6$ is a substituted or unsubstituted alkylene or cycloalkylene group; $R^7$ is hydroxyl, alkoxy, aryloxy, or $G^2$; $R^8$ is hydroxyl, alkoxy, aryloxy, or $G^3$; $G^1$, $G^2$, and $G^3$ are each independently an oxygen atom of the glass fiber, where $G^1$, $G^2$, and $G^3$ are not the same oxygen atom; and $Y^-$ is a sulfate, bisulfate, sulfonate, halide, carboxylate, phosphate, phosphonate, dicyanamide anion, perfluoroalkylsulfonate, perfluoroalkylsulfonamide anion, or bis(perfluoroalkylsulfonyl)imide anion. Thus, the at least one structural unit according to Formula IIa may be disposed on the surface of the glass fiber. In some embodiments, $R^4$ and $R^5$ are each independently H or a substituted or unsubstituted alkyl or cycloalkyl group; and $R^6$ is a substituted or unsubstituted alkylene or cycloalkylene group. In some embodiments, $R^4$ and $R^5$ are each independently H or an unsubstituted alkyl or cycloalkyl group; and $R^6$ is an unsubstituted alkylene or cycloalkylene group. In some embodiments, $R^4$ and $R^5$ are each independently H or an unsubstituted alkyl group; and $R^6$ is an unsubstituted alkylene group. In some embodiments, $R^4$ and $R^5$ are each independently H or an unsubstituted alkyl group; $R^6$ is an unsubstituted alkylene group; $R^7$ is hydroxyl, alkoxy, or $G^2$; and $R^8$ is hydroxyl, alkoxy, or $G^3$. In some embodiments, $Y^-$ is triflate, hexafluorophosphate, a perfluoroalkylsulfonate, or triflamide anion. In some embodiments, $X^-$ and $Y^-$ are each the same, e.g., $X^-$ is triflate and $Y^-$ is triflate, with $X^-$ and $Y^-$ being different triflate molecules. In some embodiments, the glass fiber membrane material includes a plurality of structural units according to Formula IIa.

In any of the above embodiments including at least one structural unit according to Formula IIa, the glass fiber membrane material may further include at least one structural unit according to Formula IIb.

Thus, the at least one structural unit according to Formula IIb may be disposed on the surface of the glass fiber. In some embodiments, the glass fiber membrane material includes a plurality of structural units according to Formula IIb.

In any of the above embodiments, the thickness of the glass fiber membrane material is from about 10 μm to about 400 μm. The thickness of the glass fiber membrane material may about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, about 250 μm, about 260 μm, about 270 μm, about 280 μm, about 290 μm, about 300 μm, about 310 μm, about 320 μm, about 330 μm, about 340 μm, about 350 μm, about 360 μm, about 370 μm, about 380 μm, about 390 μm, or about 400 μm as well as any range including and in between any two of these values. It is also appreciated that when such membranes are included in a sensor (or in certain membrane electrode assemblies) they are typically compressed and thus have a smaller thickness than when uncompressed. For example, in some embodiments the thickness of the glass fiber membrane material in the sensor, such as the electrochemical carbon monoxide sensor discussed herein, is from about 10 μm to about 250 μm when compressed in a sensor housing. The thickness of the compressed glass fiber membrane material may about 10 μm, about 20 μm, about 30 μm, about 40 μm, about 50 μm, about 60 μm, about 70 μm, about 80 μm, about 90 μm, about 100 μm, about 110 μm, about 120 μm, about 130 μm, about 140 μm, about 150 μm, about 160 μm, about 170 μm, about 180 μm, about 190 μm, about 200 μm, about 210 μm, about 220 μm, about 230 μm, about 240 μm, or about 250 μm as well as any range including and in between any two of these values. In some embodiments, the glass fiber membrane is compressed and has a thickness of about 75 μm to about 200 μm.

In some embodiments, the membrane material includes a polymer membrane material such as the previously described expanded PTFE, polypropylene, a polystyrene, a polyamide, a polybenzimidazole, and/or a tetrafluoroethylene-perfluoroalkylvinylether wherein the polymer membrane material optionally includes sulfonic acid groups, carboxylate groups, phosphate groups, phosphonate groups, or combinations of any two or more thereof. In some embodiments, the polymer membrane material includes sulfonic acid groups, carboxylate groups, phosphate groups, phosphonate groups, or combinations of any two or more thereof. In some embodiments, the polymer membrane material includes polystyrene sulfonic acid. In some embodiments, the polymer membrane material includes a tetrafluoroethylene-perfluoroalkylvinylether copolymer wherein the copolymer includes sulfonic acid groups and/or carboxylate groups. In some embodiments, the polymer membrane material includes a tetrafluoroethylene-perfluoroalkylvinylether copolymer wherein the copolymer includes sulfonic acid groups. The thickness of such polymer membrane materials may be about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, about 250 µm, about 260 µm, about 270 µm, about 280 µm, about 290 µm, about 300 µm, about 310 µm, about 320 µm, about 330 µm, about 340 µm, about 350 µm, about 360 µm, about 370 µm, about 380 µm, about 390 µm, or about 400 µm as well as any range including and in between any two of these values. It is also appreciated that when such membranes are included in a sensor (or in membrane electrode assemblies described herein) they are typically compressed and thus have a smaller thickness than when uncompressed. For example, in some embodiments the thickness of the polymer membrane material in a sensor, such as the electrochemical carbon monoxide sensor discussed herein, is from about 10 µm to about 250 µm when compressed in a sensor housing. The thickness of the compressed glass fiber membrane material may about 10 µm, about 20 µm, about 30 µm, about 40 µm, about 50 µm, about 60 µm, about 70 µm, about 80 µm, about 90 µm, about 100 µm, about 110 µm, about 120 µm, about 130 µm, about 140 µm, about 150 µm, about 160 µm, about 170 µm, about 180 µm, about 190 µm, about 200 µm, about 210 µm, about 220 µm, about 230 µm, about 240 µm, or about 250 µm as well as any range including and in between any two of these values (e.g., the polymer membrane material may be compressed and have a thickness of about 75 µm to about 200 µm).

The weight percent (wt %) of the protonic ionic liquid in the membrane may be about 10 wt %, about 20 wt %, about 30 wt %, about 40 wt %, about 50 wt %, about 60 wt %, about 70 wt %, about 80 wt %, or about 90 wt % of the total weight of the membrane, as well as any range including and in between any two of these values. For example, in any of the above embodiments, it may be that membrane includes a polymer membrane material and has from about 20 wt % to about 60 wt % of the protonic ionic liquid. As another example, in any of the above embodiments, it may be that the membrane includes a glass fiber membrane material and has from about 60 wt % to about 90 wt % of the protonic ionic liquid. In any of the above embodiments, it may be that the membrane includes a glass fiber membrane material and has from about 70 wt % to about 90 wt % of the protonic ionic liquid. In any of the above embodiments, it may be that the membrane does not include a polymer.

In any of the above embodiments, it may be that the membrane is an ion exchange membrane. In any of the above embodiments, it may be that the membrane is a proton conducting membrane.

In an aspect, a membrane electrode assembly is provided that includes an anode; a cathode that includes an oxygen reduction catalyst; and any of the above embodiments of a membrane of the present technology. The membrane permits ion transport (e.g., hydrogen ions (protons), hydroxide ions, carbonate ions) between the anode and the cathode, and prevents electron conduction between the anode and the cathode. In some embodiments, the anode and the cathode of the membrane electrode assembly are disposed upon opposite sides of the membrane and/or exposed to a different gaseous environment (e.g., a first configuration). In some embodiments, the anode and the cathode of the membrane electrode assembly are disposed upon the same side of the membrane and/or exposed to the same gaseous environment (e.g., a second configuration).

In an aspect, an electrochemical carbon monoxide sensor for use in a gas or fire detector is provided. The sensor includes a first sidewall; a second sidewall; a top wall; and a bottom wall; the first sidewall, the second sidewall, the top wall and the bottom wall defining a containment region and containing therein a membrane electrode assembly; where the top wall includes a gaseous diffusion aperture; the membrane electrode assembly includes an anode, a cathode, and any of the above embodiments of a membrane of the present technology; where the membrane permits ion transport between the anode and the cathode, the membrane prevents electron conduction between the anode and the cathode; the cathode includes an oxygen reduction catalyst. In some embodiments of the sensor, the containment region is void of a solvent reservoir. In some embodiments of the sensor, the electrochemical carbon monoxide sensor is configured to be exposed to a sample gas during a normal sensing operation; and the anode and cathode are configured to be exposed to the same sample gas at the same time during the normal sensing operation.

In any of the above embodiments of the membrane electrode assembly or the sensor, the oxygen reduction catalyst may include a pyrolysis product of a carbonaceous material and a coordination complex, the coordination complex including a transition metal and a nitrogen-containing macrocycle; where the oxygen reduction catalyst does not materially exhibit catalytic activity for the oxidation of carbon monoxide. Such electrochemically selective catalysts enables wherein the anode and the cathode of the membrane electrode assembly are disposed upon opposite sides of the membrane and/or exposed to different gaseous environments, as well as configurations wherein the anode and the cathode of the membrane electrode assembly are disposed upon the same side of the membrane and/or exposed to the same gaseous environment. The oxygen reduction catalysts may be heat treated, pyrolyzed, and/or otherwise activated in a manner which enables the catalysts to remain functionally operable and stable.

In some embodiments, the coordination complex is a transition metal porphyrin, a transition metal tetrabenzoporphyrin, a transition metal tetraphenylporphyrin, a transition metal tetraazaporphyrin, a transition metal tetraazamacrocycle, a transition metal phthalocyanine, a transition metal naphthalocyanine, a transition metal bis(phthalocyanine), a transition metal bis(naphthalocyanine), a ion metal bis(naphthalocyanines), or a combination of any two or more thereof. In some embodiments, the coordination complex is a cobalt porphyrin, a cobalt tetrabenzoporphyrin, a cobalt tetraphenylporphyrin, a cobalt tetraazaporphyrin, a cobalt tetraazamacrocycle, a cobalt metal phthalocyanine, a cobalt naphthalocyanine, a cobalt bis(phthalocyanine), a cobalt bis(naphthalocyanine), or a combination of any two or more thereof. In some embodiments, the coordination complex includes a compound of a transition metal ligated by a tetraazamacrocycle.

In some embodiments, the coordination complex is a compound represented by Formula III-VII, or a combination of any two or more thereof:

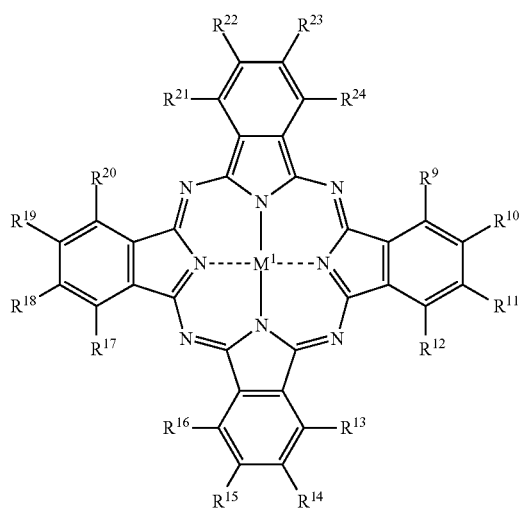

(III)

where $M^1$ is Co, Cu, Fe, Ir, Ni, Pd, Rh, Ru, or Zn; $R^9$-$R^{24}$ are each independently H, $NO_2$, $NH_2$, an amine, $CO_2H$, an ester, a $C_1$-$C_{10}$ alkyl, an ether, SH, or a thioether;

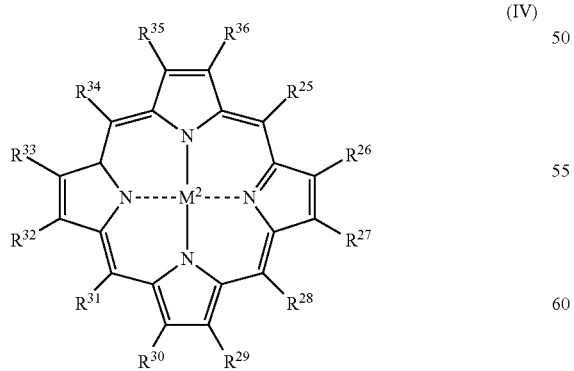

(IV)

where $M^2$ is Co, Cu, Fe, Ir, Ni, Pd, Rh, Ru, or Zn; $R^{25}$-$R^{36}$ are each independently H, $NO_2$, $NH_2$, an amine, $CO_2H$, an ester, a $C_1$-$C_{10}$ alkyl, an ether, SH, or a thioether;

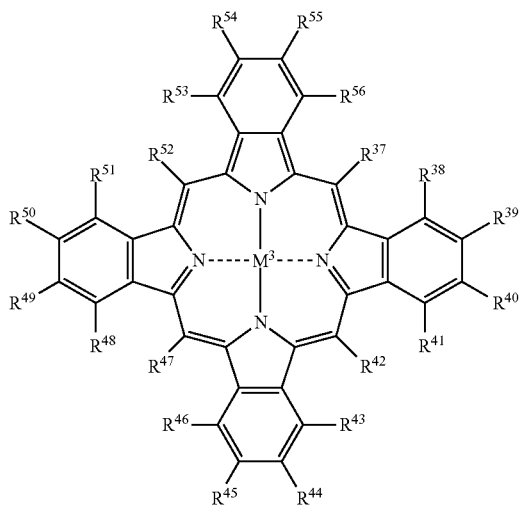

(V)

where $M^3$ is Co, Cu, Fe, Ir, Ni, Pd, Rh, Ru, or Zn; $R^{37}$-$R^{56}$ are each independently H, $NO_2$, $NH_2$, an amine, $CO_2H$, an ester, a $C_1$-$C_{10}$ alkyl, an ether, SH, or a thioether;

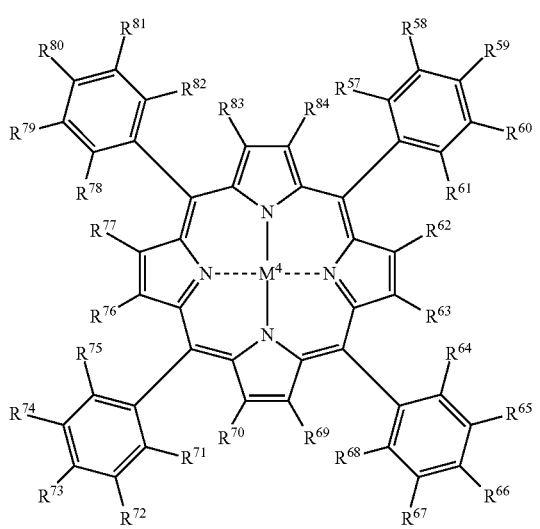

(VI)

where $M^4$ is Co, Cu, Fe, Ir, Ni, Pd, Rh, Ru, or Zn; $R^{57}$-$R^{84}$ are each independently H, $NO_2$, $NH_2$, an amine, $CO_2H$, an ester, a $C_1$-$C_{10}$ alkyl, an ether, SH, or a thioether; and

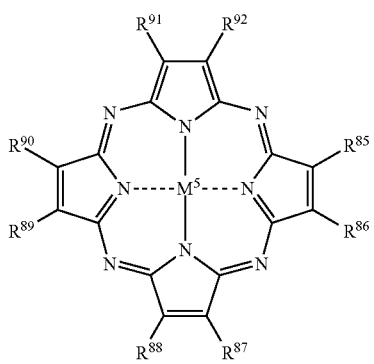

(VII)

where $M^5$ is Co, Cu, Fe, Ir, Ni, Pd, Rh, Ru, or Zn; $R^{85}$-$R^{92}$ are each independently H, $NO_2$, $NH_2$, an amine, $CO_2H$, an ester, a $C_1$-$C_{10}$ alkyl, an ether, SH, or a thioether.

In some embodiments, the coordination complex is a compound represented by Formula III. In some embodiments, the coordination complex is a compound represented by Formula III, $M^1$ is Co, and $R^9$-$R^{24}$ are each independently H. In some embodiments, the coordination complex is a compound represented by Formula III, $M^1$ is Co; and $R^9$-$R^{24}$ are each independently H, $NO_2$, or $NH_2$. In some embodiments, the coordination complex is a compound represented by Formula III, $M^1$ is Co; and $R^9$-$R^{24}$ are each independently H or $NH_2$. In some embodiments, the coordination complex is a compound represented by Formula III, $M^1$ is Co; and $R^9$-$R^{24}$ are each independently H or $NO_2$. In some embodiments, the coordination complex is a compound represented by Formula III, $M^1$ is Co; $R^{11}$, $R^{15}$, $R^{19}$, and $R^{23}$ are each independently $NH_2$; and $R^9$, $R^{10}$, $R^{12}$, $R^{13}$, $R^{14}$, $R^{16}$, $R^{17}$, $R^{18}$, $R^{20}$, $R^{21}$, $R^{22}$, and $R^{24}$ are each independently H. In some embodiments, the coordination complex is a compound represented by Formula III, $M^1$ is Co; $R^{11}$, $R^{15}$, $R^{19}$, and $R^{23}$ are each independently $NO_2$; and $R^9$, $R^{10}$, $R^{12}$, $R^{13}$, $R^{14}$, $R^{16}$, $R^{17}$, $R^{18}$, $R^{20}$, $R^{21}$, $R^{22}$, and $R^{24}$ are each independently H.

In any of the above embodiments of the membrane electrode assembly or the sensor, the carbonaceous material may include graphene, graphite, amorphous carbon, carbon nanotubes, carbon fibers, or a combination of any two or more thereof. The carbon nanotubes include, for example, single walled nanotubes (SWNT), double walled nanotubes (DWNT), and multi-walled nanotubes (MWNT), all of which may optionally be doped with atoms including, but not limited to, nitrogen, boron, and/or phosphorous.

In any of the above embodiments of the sensor, the sensor may further include a desiccant for retaining a liquid. In such embodiments, the liquid may include water. The sensor may further include a configuration to prevent water from freezing, such as the inclusion of antifreeze or salts. In any of the above embodiments, the sensor may include a configuration that is at least substantially waterless, where "substantially waterless" is well known to a person of ordinary skill in the art, such as where the water included in the desiccant is nonflowing upon forming the desiccant or that the sensor does not include a desiccant for retaining a liquid.

Numerous electrochemical sensor/cell designs and configurations are contemplated for use with the present technology, including those disclosed in U.S. Pat. No. 4,329,214 entitled "Gas Detection Unit," U.S. Pat. No. 5,302,274 entitled "Electrochemical Gas Sensor Cells Using Three Dimensional Sensing Electrodes," U.S. Pat. No. 5,331,310 entitled "Amperometric Carbon Monoxide Sensor Module for Residential Alarms," U.S. Pat. No. 5,573,648 entitled "Gas Sensor Based on Protonic Conductive Membranes," U.S. Pat. No. 5,618,493 entitled "Photon Absorbing Bio-derived Organometallic Carbon Monoxide Sensors," U.S. Pat. No. 5,650,054 entitled "Low Cost Room Temperature Electrochemical Carbon Monoxide and Toxic Gas Sensor with Humidity Compensation Based on Protonic Conductive Membranes," U.S. Pat. No. 5,944,969 entitled "Electrochemical Sensor With A Non-Aqueous Electrolyte System," U.S. Pat. No. 5,958,200 entitled "Electrochemical Gas Sensor," U.S. Pat. No. 6,172,759 entitled "Target Gas Detection System with Rapidly Regenerating Optically Responding Sensors," U.S. Pat. No. 6,200,443 entitled "Gas Sensor with a Diagnostic Device," U.S. Pat. No. 6,936,147 entitled "Hybrid Film Type Sensor," U.S. Pat. No. 6,948,352 entitled "Self-Calibrating Carbon Monoxide Detector and Method," U.S. Pat. No. 7,077,938 entitled "Electrochemical Gas Sensor," U.S. Pat. No. 7,022,213 entitled "Gas Sensor and its Method of Manufacture," U.S. Pat. No. 7,236,095 entitled "Solid State Sensor for Carbon Monoxide," U.S. Pat. No. 7,279,081 entitled "Electrochemical Sensor," U.S. Pat. No. 8,641,878 entitled "Cathodic Materials for Use in Electrochemical Sensors and Associated Devices and Methods of Manufacturing the Same," U.S. Patent Publication No. 2005/0145494 entitled "Liquid Electrochemical Gas Sensor," U.S. Patent Publication No. 2006/0091007 entitled "Gas Detecting Device with Self-Diagnosis for Electrochemical Gas Sensor," U.S. Patent Publication No. 2006/0120924 entitled "Proton Conductor Gas Sensor," and U.S. Patent Publication No. 2006/0196770 entitled "Liquid Electrochemical Gas Sensor," each of which are hereby incorporated herein by reference in their entirety—including all references cited therein. In addition, the membrane electrode assembly may be fabricated using any one of a number of conventional techniques, including pad or decal printing, as is disclosed in U.S. Pat. Nos. 5,211,984 and 8,641,878, each of which is hereby incorporated herein by reference in their entireties including all references cited therein.

In addition, in some embodiments the sensors of the present technology preferably comply with alarm specifications set forth in UL 2034.

The examples herein are provided to illustrate advantages of the present technology and to further assist a person of ordinary skill in the art with preparing or using the present technology. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

EXAMPLES

It will be understood that, unless otherwise specified, the chemical reagents and compounds provided herein below, or their precursors, are available from common commercial chemical vendors, such as Sigma-Aldrich Chemical Co., of Milwaukee, Wis., U.S.A.

Example 1. Preparation of a
Diethylmethylammonium Triflate (DEMA.OTf)
Protonic Ionic Liquid A dry 350 mL Schlenk flask was placed under nitrogen, charged with trifluoromethanesulfonic acid ("triflic acid,"

50.0 g, 333 mmol, Sigma-Aldrich, 98%). The flask was cooled in a dry ice/isopropanol bath. Diethylmethylamine ("DEMA," 29.3 g, 336 mmol, Sigma-Aldrich, 98%) was added dropwise to the flask with gentle stirring. The initial reaction was vigorous but subsided as a buffer layer of the ionic liquid formed between the dense triflic acid and the amine. The remainder of the amine was added and the mixture stirred until only one layer remained. After 30 minutes, the flask was heated to 80° C. under vacuum to remove volatile starting materials. The product was diluted with 120 mL methanol and decolorized with Darco Norit G60 carbon. The carbon was removed by filtration and the methanol removed by rotary evaporation. The final DEMA.OTf product was stored under nitrogen.

Example 2. Oxygen Reduction Activity of Pt in DEMA.OTf

The reference electrode was Ag/AgCl. Counter electrode was Pt mesh. The electrolyte was 2.0 mL DEMA.OTf which was initially purged with argon for 30 minutes then a blanket of argon maintained over the electrolyte. The working electrode was a 1.5 mm diameter Pt button. After stabilization of the signal by cycling the potential five times from 1.0 V to −0.2 V at 50 mV/s, the solution was purged with oxygen for 2 minutes then a blanket of oxygen maintained over the electrolyte. The catalytic activity was determined by scanning the potential from 1.0 V to −0.8 V at 10 mV/s. Activity is determined by the onset of current. FIG. 1 provides the results of these experiments.

Example 3. Oxygen Reduction Activity of Co*XC72R in DEMA.OTf

The reference electrode was Ag/AgCl. Counter electrode was Pt mesh. The electrolyte was 2.0 mL DEMA.OTf which was purged with argon for 30 minutes then a blanket of argon maintained over the electrolyte. The catalyst solution was prepared by dispersing 5.0 mg Co*XC72R (see Example 11) in 10.00 g $H_2O$ (Millipore) via sonication (Sonics VC750, ⅛" tip, 10 minutes total "on" time, 30 s on/10 s off pulse, 30% amplitude) with cooling in an ice bath. 40 µL of 5% Nafion solution was added to the suspension as a binder. The suspension was sonicated for an additional 5 minutes as above. The working electrode was prepared by depositing 1.8 µL of the suspension on a 1.5 mm diameter glassy carbon electrode followed by drying. A blank was run by cycling the potential from 1.0 V to −0.8 V at 10 mV/s under argon. The solution was then purged with oxygen for 2 minutes then a blanket of oxygen maintained over the electrolyte. The catalytic activity was determined by scanning the potential from 1.0 V to −0.8 V at 10 mV/s. Activity is determined by the onset of current. FIG. 1 provides the results of these experiments. Notably, the oxygen reduction activity of Co*XC72R in the DEMA.OTf electrolyte is much higher than that of the platinum catalyst.

Example 4. Carbon Monoxide Oxidation Activity in DEMA.OTf with Pt Catalyst

Figure 2:
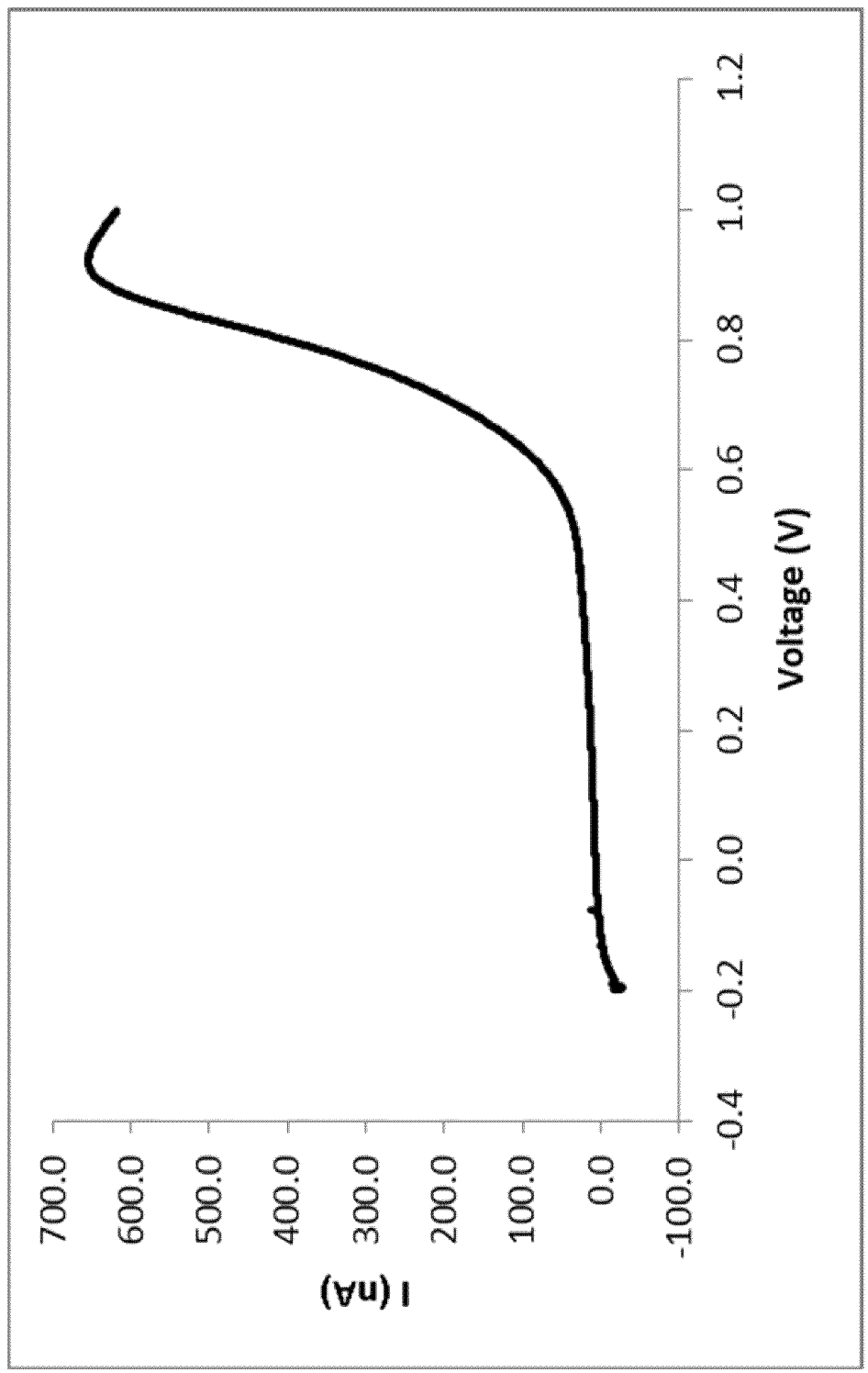
FIG. 2 illustrates the initial activity for the oxidation of carbon monoxide ("CO") in a protonic ionic liquid of the present technology with a platinum catalyst, according to a working example.

This example was run similarly to Examples 2 & 3, except the solution was purged with carbon monoxide for two minutes then a blanket of carbon monoxide maintained over the electrolyte. The catalytic activity was determined by scanning the potential from −0.2 to 1.0V at 10 mV/s. Activity is determined by the onset of current. FIG. 2 provides the results of these experiments and shows good catalytic activity for the oxidation of CO.

Example 5. Preparation of Ammoniated Borosilicate Glass Fiber Membranes (GFN+)

Borosilicate glass microfiber ("GF") membranes (9.0 cm diameter, 300 µm thick, VWR Brand 696) were dried at 70° C. for a minimum of 24 hours. The membranes were soaked in a 20 mM solution of N,N-dimethylaminopropyltrimethoxysilane (Gelest Chemicals) in 98% aqueous ethanol for four hours. The membranes were removed and excess solvent allowed to evaporate. The membranes were then heated to 120° C. for 80 minutes to complete the silanization process. A 40 mM solution of triflic acid in anhydrous acetonitrile was prepared under an argon atmosphere. The silanized membranes were soaked in the triflic acid solution for two hours. The membranes were then removed, excess solvent removed by suction, and rinsed with three aliquots of anhydrous acetonitrile until the filtrate was pH neutral. The GFN+ membranes were then dried under nitrogen at 60° C. for a minimum of five hours.

Example 6. Preparation of GFN+/DEMA.OTf Proton Conducting Membrane

A composite PEM was prepared by addition of DEMA.OTf to the GFN+ membranes at a level of 20-25 mg/cm² DEMA.OTf to GFN+ membrane area. While for this particular series the best shaped signal was provided at levels of about 20-25 mg/cm², addition of DEMA.OTf to the GFN+ membranes at a levels of 10-50 mg/cm² worked well, with more favorable signal provided in the range of 15-30 mg/cm².

Example 7. Preparation of Nafion-DEMA/DEMA.OTf Proton Conducting Membrane

Membranes of Nafion XL (Dupont) were purified by boiling in 2M $HNO_3$ for 90 minutes. The Nafion was removed and washed with $H_2O$ (18.2 MΩ-cm, Millipore RO water) until the filtrate was pH neutral. The membranes were then converted to the DEMA+ form by soaking in a 1M diethylmethylamine in 1:1 ethanol/$H_2O$ for 16 hours. They were rinsed with deionized $H_2O$ until the filtrate was pH neutral then dried for 48 hours at 80° C. The membranes were then doped in a DEMA.OTf for 16 hours at 80° C. under nitrogen. The membrane was removed, excess liquid was wiped from the surface and the membrane stored under nitrogen until use. The membrane was 40 wt % DEMA.OTf based on the total weight of the Nafion-DEMA/DEMA.OTf.

Example 8. Preparation of Phosphoric Acid-Polybenzimidazole/GF (PA-PBI/GF) Proton Conducting Membranes GF membranes (9.0 cm diameter, 300 µm thick, VWR Brand 696) were dried at 70° C. for a minimum of 2 hours. The GF membranes were soaked in a solution of 5% polybenzimidazole ("PBI") (PBIS26 w/LiCl stabilizer, PBI Performance Products, Inc.) in dimethyl acetamide (DMAc) overnight. The soaking membranes were alternated between light vacuum and ambient pressure to remove air bubbles from the GF membrane. The membranes were removed from the solution and suspended vertically to drain excess PBI solution. The membranes were subsequently dried at 120° C. under nitrogen for 3 hours. LiCl was removed by boiling the membranes in deionized $H_2O$ for 2 hours. The water was changed 3 times during the boiling period. The membranes were then dried under nitrogen for 3 hours at 90° C. followed by doping in 85% $H_3PO_4$ ("PA," GFS Chemicals, 99.999%) for 14 hours at room temperature. Excess acid was removed by suction and the PA-PBI/GF membranes dried under nitrogen at 90° C.

Example 9. Preparation of PA/FumaPEM AM-55 Proton Conducting Membrane

Polybenzimidazole membranes (FumaPEM AM-55, FumaTech GmBH) were soaked in 85% $H_3PO_4$ (GFS Chemicals, 99.999%) for 5.5 hours at room temperature. The doped membranes were removed from the 85% $H_3PO_4$ and excess acid was removed from the surface by rolling the membrane between HDPE rollers.

Example 10. Preparation of Pt-XC72/Nafion(BuAc) Ink for Anode

A 4 ounce amber vial was charged with 88.5 parts n-butyl acetate and 1.5 parts 40% Pt-XC72 (Alfa Aesar). The suspension was homogenized at 10 k rpm with an IKA T-25 homogenizer for 60 minutes. A solution of 3.33 parts Nafion (15 wt %, Ion-Power) in 6.67 parts 2-propanol was added dropwise to the suspension over two minutes. The suspension was then homogenized for an additional 15 minutes. Agitation was maintained until use.

Example 11. Preparation of Co*XC72R/Nafion(BuAc) Ink for Cathode i. Preparation of Co*XC72: A 1-L conical bottom flask was charged with 3.04 g carbon black (Vulcan® XC72R carbon, Cabot Corp.) in 300 mL DMF. The suspension was bubbled with argon for 10 minutes then an argon blanket was maintained over the suspension. The carbon was dispersed into the solvent by sonication (Sonics VC750, 1" tip, 30 minutes total "on" time, 30 s on/10 s off pulse, 70% amplitude) while cooled in an ice bath. 2,9,16,23-tetranitrophthalocyanine cobalt ("CoPc($NO_2$)$_4$", 1.52 g) in 150 mL DMF was added to the carbon suspension. Sonication was repeated under the above conditions for 10 minutes of total "on" time. The suspension was then stirred at room temperature for 48 hours. The DMF was removed by rotary evaporation and dried under vacuum at 75° C. for 2 hours. The solid was then transferred to a fused quartz boat and placed in a tube furnace under argon flow (400 mL/min) for 1 hour at 150° C. The argon flow was reduced to 100 mL/min and then temperature ramped to 700° C. and held for two hours. The temperature was cooled to RT and the resulting solid finely ground with mortar and pestle. Final yield of pyrolyzed 33 wt. % CoPc($NO_2$)$_4$ on XC72 (Co*XC72R) was 3.94 g (86%)

ii. Preparation of the ink: 4 ounce amber vial was charged with 82.75 parts n-butyl acetate and 2.25 parts Co*XC72R. The suspension was homogenized at 10,000 rpm with an IKA T-25 homogenizer for 60 minutes. A solution of 5 parts Nafion (15 wt %, Ion-Power) in 10 parts 2-propanol was added dropwise to the suspension over two minutes. The suspension was then homogenized for an additional 15 minutes. Agitation was maintained until use.

Example 12. Preparation of Pt-XC72R/Nafion(BuAc) Gas Diffusion Electrode (GDE)

Pt-XC72R/Nafion(BuAc) ink was diluted to approximately 1 wt % solids with additional n-butyl acetate. The ink was applied to Avcarb P50T carbon paper using an airbrush. A coverage of 0.116 mg/cm$^2$ (0.035 mg/cm$^2$ Pt) was achieved by several passes of the airbrush followed by drying at 70° C. under nitrogen for two hours. A flash coat of 5% Nafion was airbrushed across the surface followed by drying as above.

Example 13. Preparation of Co*XC72R/Nafion(BuAc) GDE

Co*XC72R/Nafion(BuAc) ink was applied to Avcarb P50T carbon paper using an airbrush. A coverage of 3.8 mg/cm$^2$ was achieved by several passes of the airbrush followed by drying at 70° C. under nitrogen for two hours. A flash coat of 5% Nafion was airbrushed across the surface followed by drying as above.

Example 14. Membrane Electrode Assembly (MEA) by Direct Application of Catalysts to GFN+/DEMA.OTf Proton Conducting Membrane Pt-XC72R/Nafion(BuAc) ink was diluted to approximately 1 wt % solids with additional n-butyl acetate. The ink applied to a GFN+ membrane using an airbrush. A coverage of 0.115 mg/cm$^2$ (0.035 mg/cm$^2$ Pt) was achieved by several passes of the airbrush followed by drying at 70° C. under nitrogen for two hours. On the opposite side of the membrane Co*XC72R/Nafion(BuAc) ink was applied using an airbrush. A coverage of 2.5 mg/cm$^2$ was achieved by several passes of the airbrush followed by drying at 100° C. under nitrogen for 16 hours. The MEA was cut or punched to a 15.9 mm outer diameter (O.D.)/3.1 mm inner diameter (I.D.) disk, then 40 mg DEMA.OTf was evenly pipetted across the surface resulting in a coverage level of 21 mg/cm$^2$. The MEA was completed by stacking with Avcarb P50T carbon paper (15.9 mm O.D./3.1 mm I.D.) on either side.

Example 15. MEA by Lamination of GDEs with a PA-PBI/GF Proton Conducting Membrane The anode GDE of Example 12 and cathode GDE of Example 13 were cut or punched to 15.9 mm O.D./3.1 mm I.D. disks. The PA-PBI/GF of Example 5 was cut or punched to 15.9 mm O.D./3.1 mm I.D. disk. These were then stacked so that the PA-PBI/GF membrane was between the anode GDE and the cathode GDE, and subsequently laminated at 8 atm at 130° C. for 2 minutes followed by cooling to room temperature.

Example 16. Preparation of Sensors

Figure 3:
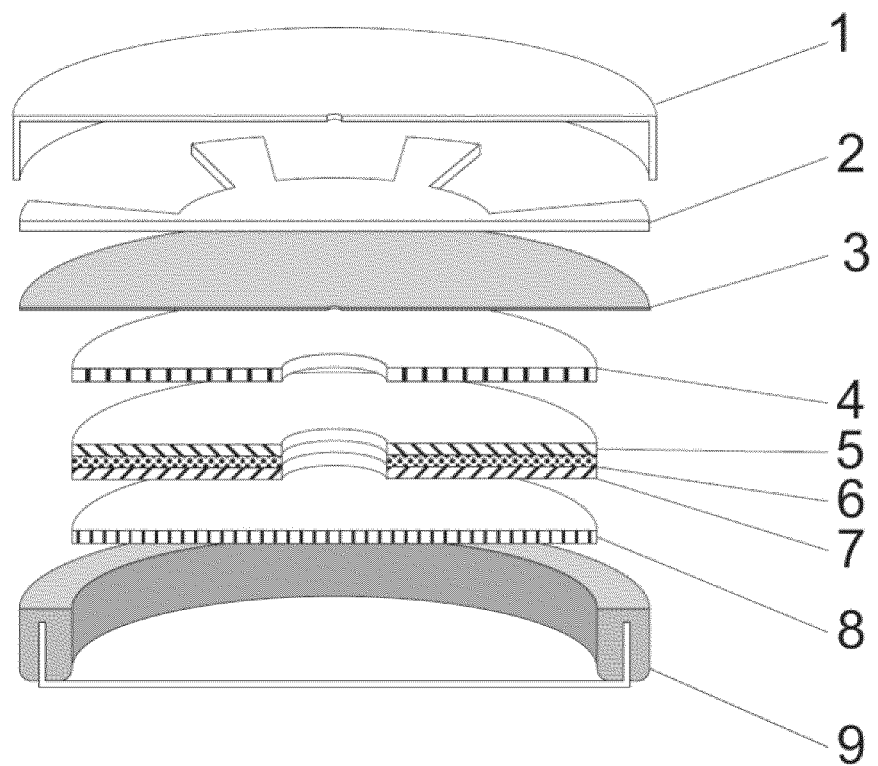
FIG. 3 illustrates the construction of a sensor, according to a working embodiment.

An off the shelf CR2016 battery case stamped from 304 or 316 stainless steel (MTI Corporation) was used for the housing. FIG. 3 illustrates the construction. 1 is the case top and sensor anode (typically cathode in a battery) with a 700 μM gas inlet drilled in the middle. 2 is a microporous PTFE filter (Porex) or expanded PTFE filter (W. L. Gore Gore-Tex) used to protect the diffusion plate hole from dust or external water. 3 is a diffusion control plate with a small gas inlet hole to prevent flooding the sensor catalysts with too high of a CO concentration. 4 is a 316SS rigid spacer (15.9 mm O.D./3.1 mm I.D.). The MEA includes an anode 5, a proton conducting membrane 6, and a cathode 7. 8 is a 316SS rigid spacer (15.9 mm O.D.). 9 is the case bottom and sensor cathode with attached seal. The parts were assembled then crimped (MTI MSK-110) at a pressure of about 50 kg/cm$^2$, although it should be noted crimping pressures of 25-75 kg/cm$^2$ are generally acceptable. Solder tabs were welded to the sensor case.

Figure 4:
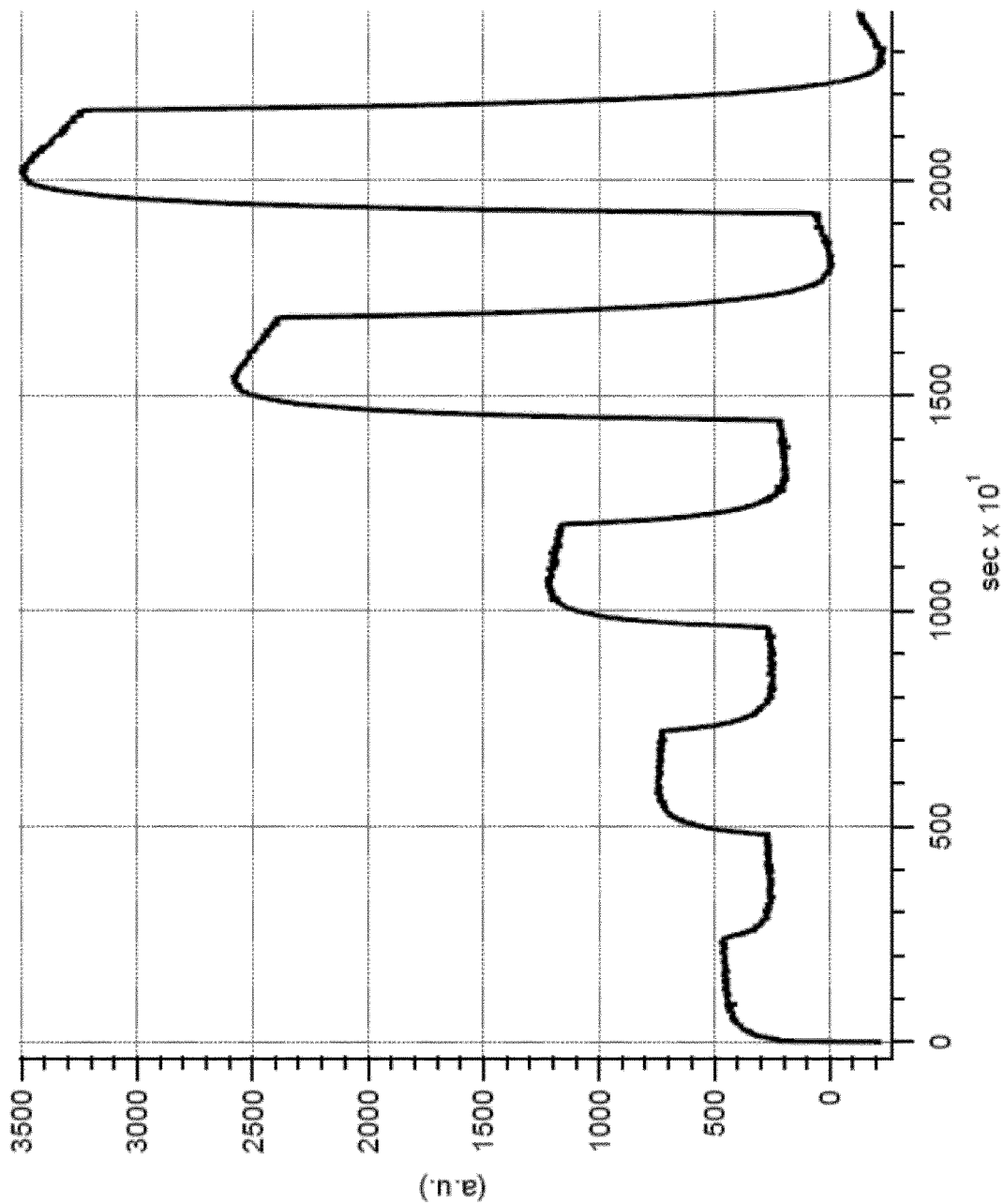
FIG. 4 illustrates the operation of a CO sensor employing a membrane of the present technology where the CO concentration is varied, according to a working example.

Example 17. Operation of a CO Sensor at Various CO Concentrations with GFN+/DEMA.OTf Membrane Sensors incorporating a GFN+/DEMA.OTf membrane from Example 6 were soldered to PCBs with an operational amplifier (op-amp) circuit for each sensor. The PCBs were placed in a home-built gas chamber with computer controlled gas environment (CO and air) and electrical feedthroughs to measure the sensor outputs. The gas chamber is sealed containing fresh air. CO of known concentration is pumped for a defined amount of time into the chamber while maintaining ambient pressure. Upon completion of the CO exposure, the chamber is evacuated and flushed with fresh air while maintaining ambient pressure. The experiment was performed by utilizing 40 minute pulses of 30, 70, 150, 400, 600 ppm CO with 40 minute pulses of air in between. The relative humidity was 45% at 23° C. FIG. 4 shows a typical sensor output with the X scale in tens of seconds (sec×10$^{-1}$) and the Y scale in arbitrary units unique to the op-amp circuit gain.

Figure 5:
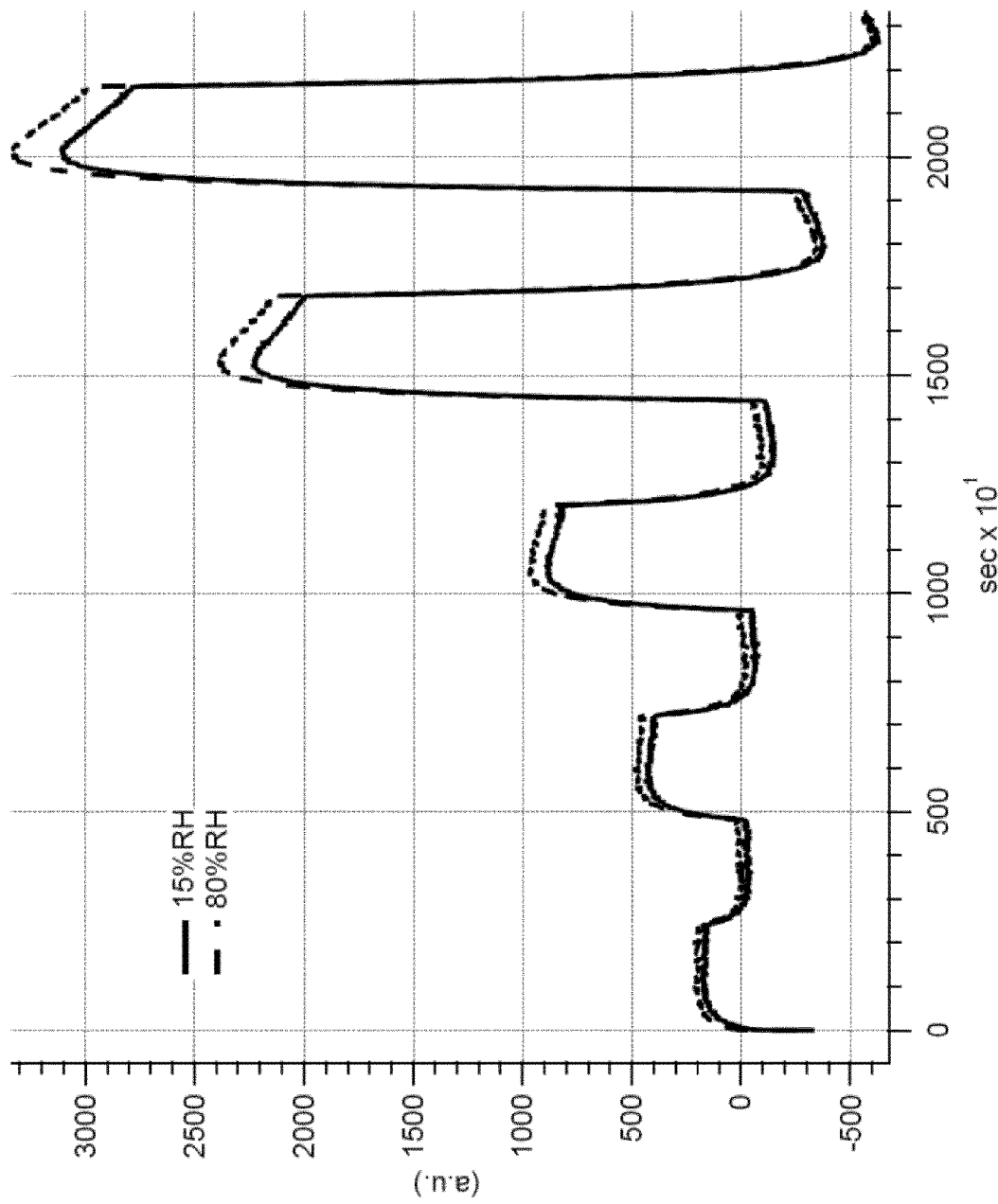
FIG. 5 illustrates the operation of a CO sensor employing a membrane of the present technology where the CO concentration and the relative humidity are varied, according to a working example.

Example 18. Operation of a CO Sensor at Various CO Concentrations and Various Humidity with Catalysts Directly Applied to GFN+/DEMA.OTf Membranes To vary the relative humidity of the gas chamber described in Example 16, various saturated salt bathes are prepared in a large 9"×13" Pyrex dish placed at the bottom of the chamber. For the high humidity experiment, the sensors were first stored for 27 hours at ~90% relative humidity (RH) in a sealed desiccator over a saturated ZnSO$_4$.7H$_2$O bath. The devices were then placed in the gas chamber containing the same bath. Though the chamber humidity dropped to 48-56% RH every time the chamber was flushed with fresh air, it quickly rebounded to a steady state value of 80% RH. For the low humidity experiment, the sensors were first stored for 96 hours at ~6% RH in a sealed desiccator over a partially saturated NaOH bath. The devices were then placed in the gas chamber containing the same bath. Though the chamber humidity increased to 35-40% RH every time the chamber was flushed with fresh air it quickly rebounded to a steady state value of 15% RH. The experiment was performed by utilizing 40 minute pulses of 30, 70, 150, 400, 600 ppm CO with 40 minute pulses of air in between as described in Example 16 at two different relative humidities. FIG. 5 compares the output results of a typical CO sensor with GFN+/DEMA.OTf membrane. The solid line represents the experiment run at a relative humidity of 15% at 23° C.; the broken line represents the experiment run at a relative humidity of 80% at 23° C.

Figure 6:
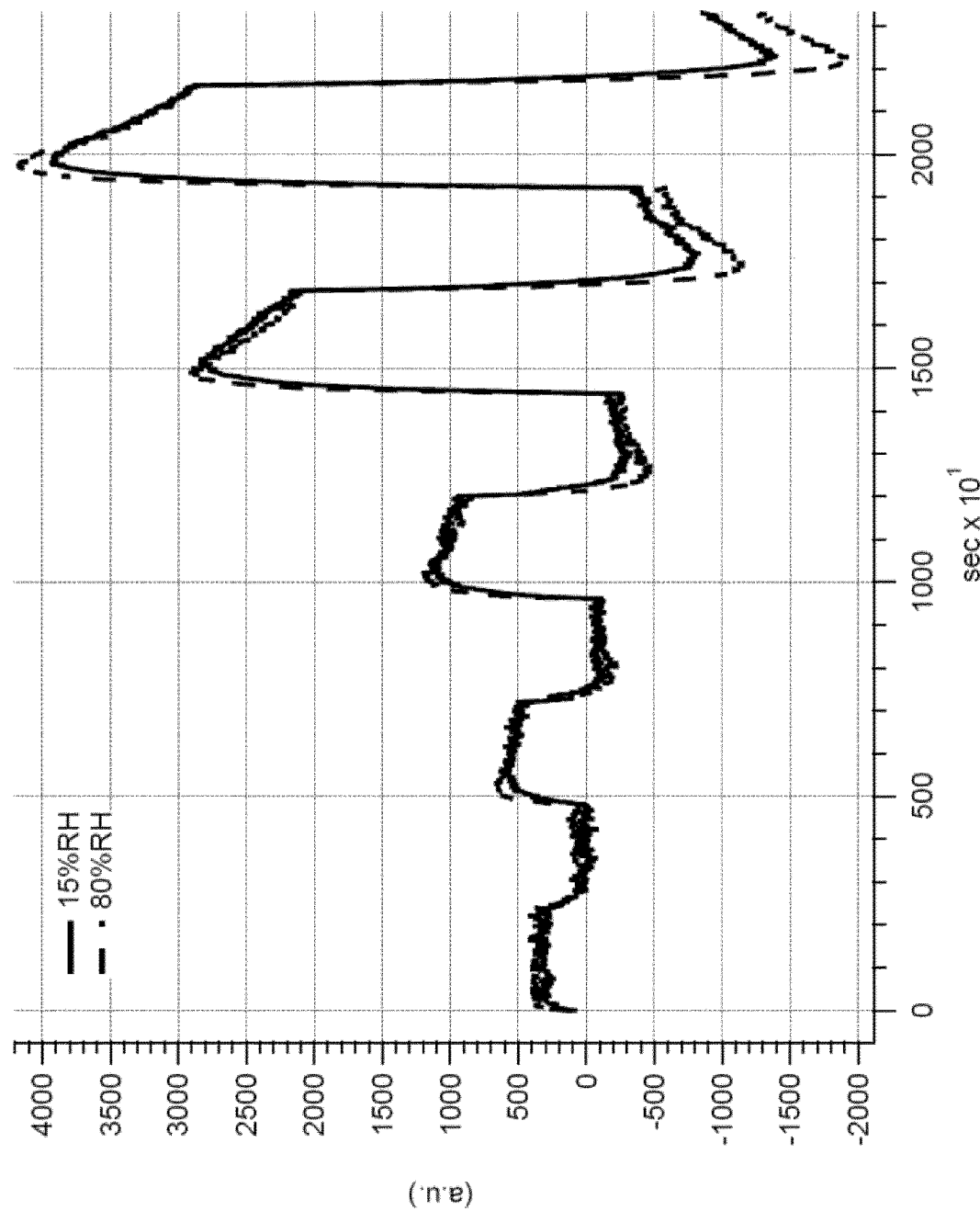
FIG. 6 illustrates the operation of a CO sensor employing a different membrane of the present technology than shown in FIG. 5 where the CO concentration and the relative humidity are varied, according to a working example.

Example 19. Operation of a CO Sensor Incorporating Nafion-DEMA/DEMA.OTf Membrane at Various CO Concentrations and Varying Humidity Using the test procedure detailed in Example 18, FIG. 6 compares the output results of a typical CO sensor with Nafion-DEMA/DEMA.OTf membrane. The solid line represents the experiment run at a relative humidity of 15% at 23° C.; the broken line represents the experiment run at a relative humidity of 80% at 23° C.

Figure 7:
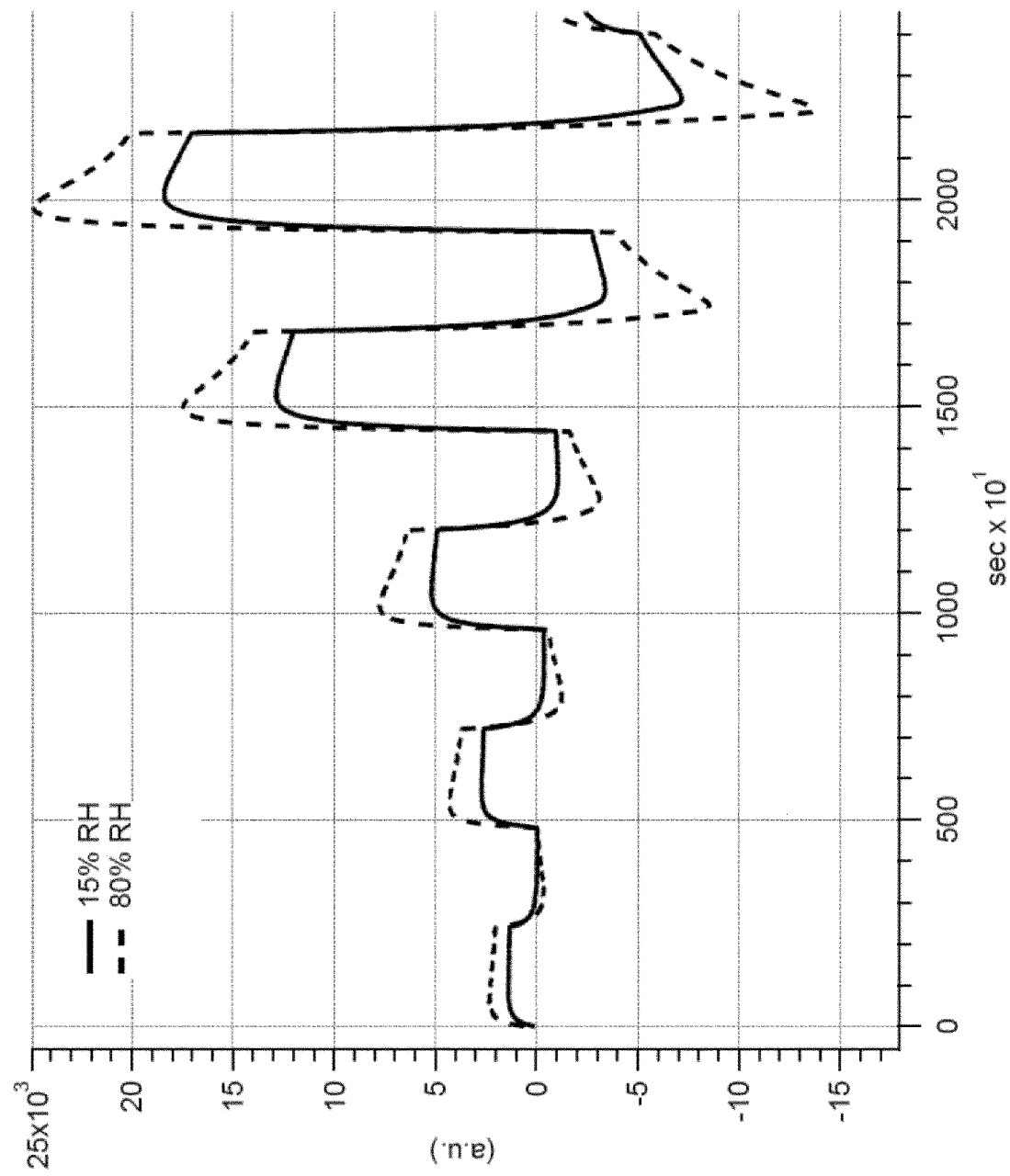
FIG. 7 illustrates the operation of a CO sensor employing a traditional ion exchange membrane not of the present technology where the CO concentration and the relative humidity are varied.

Example 20. Operation of a CO Sensor Incorporating a PA-PBI/GF Membrane at Various CO Concentrations and Varying Humidity Using the test procedure detailed in Example 18, FIG. 7 compares the output results of a typical CO sensor with PA-PBI/GF membrane. The solid line represents the experiment run at a relative humidity of 15% at 23° C.; the broken line represents the experiment run at a relative humidity of 80% at 23° C.

Figure 8:
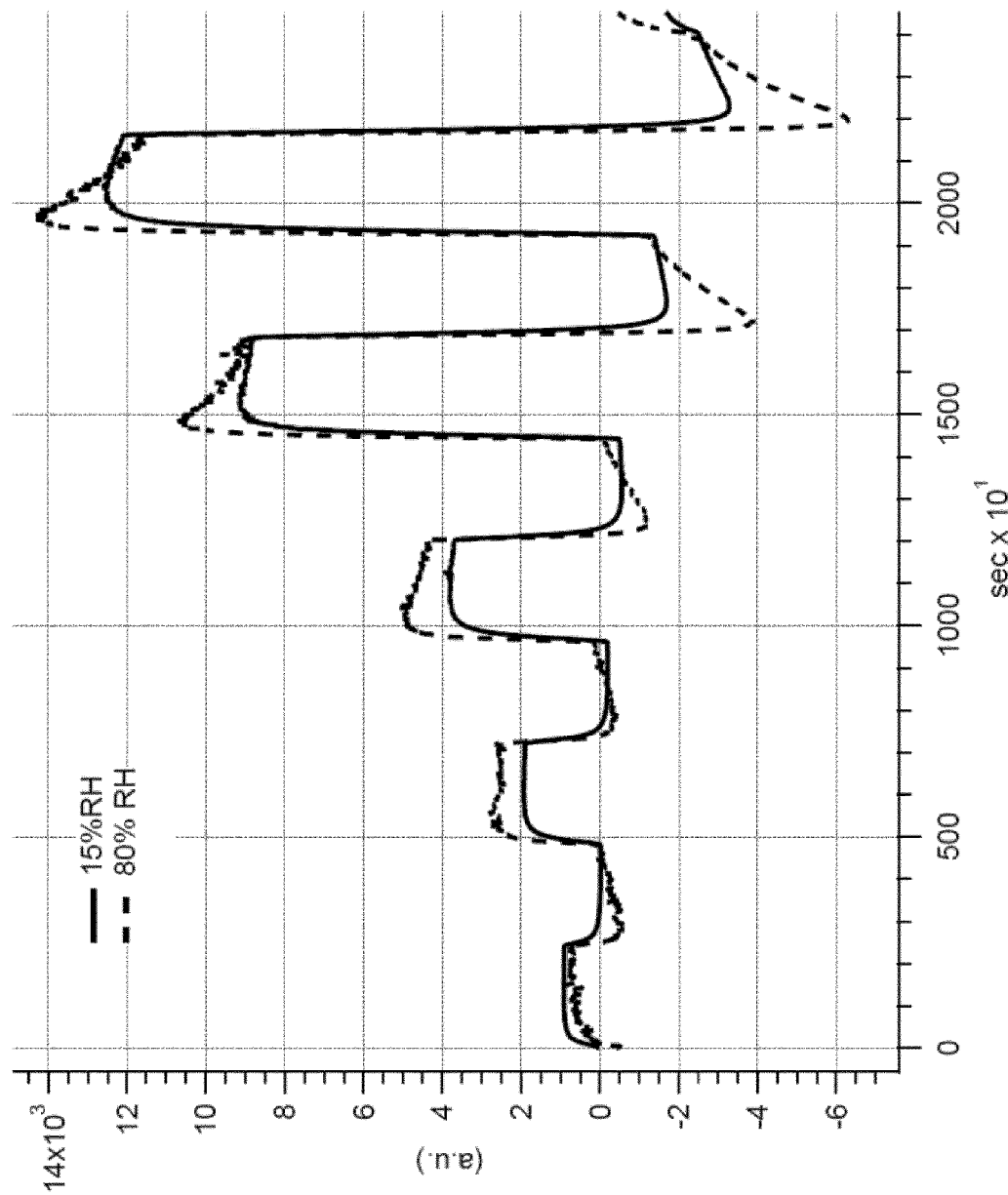
FIG. 8 illustrates the operation of a CO sensor employing a traditional ion exchange membrane not of the present technology where the CO concentration and the relative humidity are varied.

Example 21. Operation of a CO Sensor Incorporating a PA-FumaPEM Membrane at Various CO Concentrations and Varying Humidity Using the test procedure detailed in Example 18, FIG. 8 compares the output results of a typical CO sensor with PA-FumaPEM membrane. The solid line represents the experiment run at a relative humidity of 15% at 23° C.; the broken line represents the experiment run at a relative humidity of 80% at 23° C.

While certain embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

What is claimed is:

1. A membrane electrode assembly comprising
an anode;
a cathode comprising an oxygen reduction catalyst; and
an ion exchange membrane comprising:
  a membrane material with a top surface and a bottom surface and comprising a glass fiber membrane material; and
  a protonic ionic liquid disposed at least between the top surface and the bottom surface of the membrane material;
wherein the protonic ionic liquid is of Formula I:

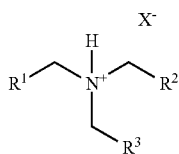

(I)

where $R^1$, $R^2$, and $R^3$ are each independently H or a substituted or unsubstituted alkyl or cycloalkyl group, or where $R^1$ and $R^2$ taken together are a $C_2$-$C_4$ alkylene group; and $X^-$ is a sulfate, bisulfate, sulfonate, halide, carboxylate, phosphate, phosphonate, dicyanamide anion, perfluoroalkylsulfonate, perfluoroalkylsulfonamide anion, or bis(perfluoroalkylsulfonyl)imide anion; and wherein the glass fiber membrane material comprises glass fibers and at least one structural unit according to Formula IIa:

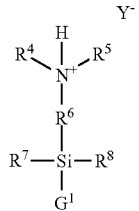

(IIa)

wherein $R^4$ and $R^5$ are each independently H or a substituted or unsubstituted alkyl or cycloalkyl group, or where $R^4$ and $R^5$ taken together are a $C_4$-$C_6$ alkylene group;

$R^6$ is a substituted or unsubstituted alkylene or cycloalkylene group;

$R^7$ is hydroxyl, alkoxy, aryloxy, or $G^2$;

$R^8$ is hydroxyl, alkoxy, aryloxy, or $G^3$;

$G^1$, $G^2$, and $G^3$ are each independently an oxygen atom of the glass fiber, where $G^1$, $G^2$, and $G^3$ are not the same oxygen atom; and $Y^-$ is a sulfate, bisulfate, sulfonate, halide, carboxylate, phosphate, phosphonate, dicyanamide anion, perfluoroalkylsulfonate, perfluoroalkylsulfonamide anion, or bis(perfluoroalkylsulfonyl)imides.

2. The membrane electrode assembly of claim 1, wherein $R^1$, $R^2$, and $R^3$ are each independently H or an unsubstituted alkyl group.

3. The membrane electrode assembly of claim 1, wherein $R^1$, $R^2$, and $R^3$ are each independently H, methyl, ethyl, n-propyl, or i-propyl.

4. The membrane electrode assembly of claim 1, wherein $X^-$ is triflate, nonafluorobutylsulfonate, or a perfluoroalkylsulfonate, or $X^-$ is a sulfonate functional group of the membrane material.

5. The membrane electrode assembly of claim 1, wherein the membrane material further comprises one or more of an expanded polytetrafluoroethylene, a polypropylene, a cellulose membrane material, a polystyrene, a polyamide, a polybenzimidazole, or a tetrafluoroethylene-perfluoroalkylvinylether, wherein the expanded PTFE, polypropylene, polystyrene, polyamide, polybenzimidazole, and/or tetrafluoroethylene-perfluoroalkylvinylether optionally includes sulfonic acid groups, carboxylate groups, phosphate groups, phosphonate groups, or combinations of any two or more thereof.

6. The membrane electrode assembly of claim 1, wherein the glass fiber membrane material further comprises at least one structural unit according to Formula IIb:

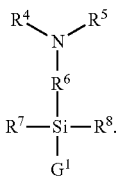
(IIb)

7. The membrane electrode assembly of claim 1, wherein $R^4$ and $R^5$ are each independently H or an unsubstituted alkyl or aryl group; and
$R^6$ is an unsubstituted alkylene group.

8. The membrane electrode assembly of claim 1, wherein $R^4$ and $R^5$ are each independently H or an unsubstituted alkyl group;
$R^6$ is an unsubstituted alkylene group;
$R^7$ is alkoxy or $G^2$; and
$R^8$ is alkoxy or $G^3$.

9. The membrane electrode assembly of claim 1, wherein the glass fiber membrane material comprises a plurality of structural units according to Formula IIa.

10. The membrane electrode assembly of claim 6, wherein the glass fiber membrane material comprises a plurality of structural units according to Formula IIb.

11. The membrane electrode assembly of claim 1, wherein a thickness defined by the top surface and the bottom surface of the membrane material is from about 10 μm to about 400 μm.

12. The membrane electrode assembly of claim 1, wherein
the membrane material further comprises a tetrafluoroethylene-perfluoroalkylvinylether copolymer wherein the copolymer comprises sulfonic acid groups.

13. The membrane electrode assembly of claim 1, wherein the ion exchange membrane has from about 20 wt % to about 90 wt % of the protonic ionic liquid.

14. The membrane electrode assembly of claim 1, wherein the ion exchange membrane further comprises an ion conducting material not of Formula I.

15. The membrane electrode assembly of claim 1, wherein the ion exchange membrane does not comprise a polymer.

16. An electrochemical carbon monoxide sensor for use in a gas or fire detector,
the sensor comprising a first sidewall; a second sidewall; a top wall; and a bottom wall; the first sidewall, the second sidewall, the top wall and the bottom wall defining a containment region and containing therein a membrane electrode assembly of claim 1;
wherein:
the top wall comprises a gaseous diffusion aperture;
the ion exchange membrane permits ion transport between the anode and the cathode; and
the ion exchange membrane prevents electron conduction between the anode and the cathode.

17. The membrane electrode assembly of claim 1, wherein the ion exchange membrane has from about 20 wt % to about 60 wt % of the protonic ionic liquid.

18. The membrane electrode assembly of claim 1, wherein the ion exchange membrane is a proton conducting membrane.

19. The membrane electrode assembly of claim 17, wherein the ion exchange membrane is a proton conducting membrane.

20. The membrane electrode assembly of claim 19, wherein the ion exchange membrane does not comprise a polymer.

* * * * *